US008012706B2

(12) United States Patent
Barale et al.

(10) Patent No.: US 8,012,706 B2
(45) Date of Patent: Sep. 6, 2011

(54) **METHODS FOR DETECTING VIRULENT *PLASMODIUM*, FOR EVALUATING *PLASMODIUM* VIRULENCE, AND FOR SCREENING NEW DRUGS EMPLOYING THE 3'UTR OF *PLASMODIUM* SUB2 AND THE *PLASMODIUM* SUB2 SERINE PROTEASE**

(75) Inventors: Jean-Christophe Barale, Paris (FR); Pierrick Uzureau, Wepion (BE); Catherine Braun-Breton, Montpellier (FR)

(73) Assignee: Institut Pasteur, Paris (FR)

( * ) Notice: Subject to any disclaimer, the term of this patent is extended or adjusted under 35 U.S.C. 154(b) by 751 days.

(21) Appl. No.: 11/119,826

(22) Filed: May 3, 2005

(65) Prior Publication Data

US 2007/0014817 A1 Jan. 18, 2007

(51) Int. Cl.
*G01N 33/53* (2006.01)

(52) U.S. Cl. ..................................................... 435/7.22

(58) Field of Classification Search ......................... None
See application file for complete search history.

(56) References Cited

U.S. PATENT DOCUMENTS

2003/0229082 A1* 12/2003 James et al. ............... 514/224.8

FOREIGN PATENT DOCUMENTS

WO WO 9613607 A1 * 5/1996
WO WO 03057723 A2 * 7/2003

OTHER PUBLICATIONS

Lahue et al., Yeast, 22:537-551, 2005.*
Nakai et al., J. Biol. Chem., 268:24262-24269, 1993.*
McDonald et al., Genetics, 171:901-911, 2005.*
Green et al., Mol. Biochem. Parasitol., 150:114-117, 2006.*
Lewin (Genes IV, 1990, Oxford Univ. Press, p. 806).*
Howell et al. (J. Biol. Chem. 278, 23890-23898, 2003.*
Uzureau et al. (Cell. Microbiol., 6:65-78, Jan. 2004).*
Barale et al. (PNAS, 96:6445-6450, 1999).*

* cited by examiner

*Primary Examiner* — Nita M Minnifield
*Assistant Examiner* — Brian J Gangle
(74) *Attorney, Agent, or Firm* — Oblon, Spivak, McClelland, Maier & Neustadt, L.L.P.

(57) ABSTRACT

Methods for regulating the serine protease of *Plasmodium*. Recombinant DNA constructs which express the *Plasmodium* serine protease, especially those comprising a sub2 3'UTR and coding segment which express a SUB2 a serine protease. Recombinant *Plasmodium* containing such constructs and exhibiting increased virulence. Methods for detecting virulent *Plasmodium* strains by detecting the presence or amount of sub2 3'UTR sequences, sub2 mRNA or cDNA, SUB2 polypeptide expression, or other *Plasmodium* proteins, such as AMA1 or MSP1, which have been post-translationally modified by SUB2.

16 Claims, 16 Drawing Sheets

METHODS FOR DETECTING VIRULENT *PLASMODIUM*, FOR EVALUATING *PLASMODIUM* VIRULENCE, AND FOR SCREENING NEW DRUGS EMPLOYING THE 3'UTR OF *PLASMODIUM* SUB2 AND THE *PLASMODIUM* SUB2 SERINE PROTEASE

REFERENCE TO SEQUENCE LISTING

This application contains a sequence listing which forms a part of the disclosure.

BACKGROUND OF THE INVENTION

1. Field of the Invention

The invention pertains to recombinant *Plasmodium* expressing the SUB2 subtilisin-like protease which has a modified non-coding 3'UTR (3 prime untranslated region). The invention also related to methods for identifying virulent strains, and/or evaluating the virulence, of *Plasmodium*, and for screening new anti-malaria drugs are disclosed.

2. Description of the Related Art

*Plasmodium* is the parasite that causes malaria. The host-parasite relationship between malaria and its host involves a complex equilibrium between parasite multiplication, which is essential for its dissemination, and host responses[1]. Collateral damage attributable to the host-parasite interaction is responsible for the disease burden, morbidity and mortality in endemic areas where malaria is a major public health problem[2].

The virulence of malaria is associated with the multiplication rate of the parasite and the ability of *Plasmodium* blood states to cytoadhere microvessels in deep organs[1,3,4]. While virulence factors involved in cytoadherence have been identified[4], those involved in high multiplication rate, for which erythrocyte invasion by merozoite is a crucial step, remain poorly understood[1,3,4].

Proteases are known to play a crucial role in various infectious diseases and cancer and have been successfully defined as chemotherapeutic targets. The specificity of protease activity permits the design of highly specific inhibitors which block a pathogenic process without considerable toxic side effects. Thus protease inhibitors are selectively toxic agents applicable for therapeutic use.

Biochemical and genetic analysis have shown that proteases and particularly serine proteases play a central role for the liberation and entry of merozoites into the host red blood cell.

Compared to intra-erythrocytic parasite states, the merozoite, as the sporozoite, is briefly free in the host plasma and therefore accessible to external factors including host immune factors like antibodies or to therapeutic drugs. The Merozoite Surface Protein 1 (MSP1) of *Plasmodium* is considered a promising candidate for a malaria vaccine. MSP1 undergoes a two step maturation process. The final processing of MSP1-42 occurs while the merozoite enters into the host RBC and is achieved by a parasite membrane-bound and calcium-dependent serine protease. Despite MSP1 polymorphism, this sequential processing is precisely conserved, even amongst different *Plasmodium* species. Even if the biological function linked to this maturation is still unknown, its inhibition using specific monoclonal antibodies or serine protease inhibitors efficiently blocks the RBC invasion.

It has recently been shown that the same parasite serine-protease is responsible for the second maturation step of the vaccine candidate Apical Membrane Antigen-1 (AMA1). Originally, AMA1 was identified to be the target of monoclonal antibodies which prevent RBC invasion by merozoites and more recently hepatocyte invasion by sporozoites. The inhibition of the maturation of AMA1 results in abortive RBC or hepatocyte invasion by the merozoites and the sporozoites, respectively.

Over the last decade, the establishment of *Plasmodium* genetic tools[7], the genome sequencing of the laboratory clone *P. falciparum* 3D7[8] and various parasite transcriptome and proteome global projects[9,10], have made profound changes in the field of malaria research. Interestingly, global expression profiling shows that 50% of the 5400 parasite genes are stage regulated, while the proportion of proteins predicted to be involved in gene regulation is low, especially when compared to *S. cerevisiae*[8]. Only a handful of regulatory elements have been identified[11,12] and none is known that controls the multigene family coding for proteins mediating cytoadherence, which are subjected to antigenic variation.

A regulatory role for the respective introns of some malaria genes and 3'UTR (3 prime untranslated region) has been recently proposed[13], as previously shown for the 3'UTR of the ookinete Pgs28 gene[14]. The 3'UTR, and particularly the addition of a polyadenylated tail, have been widely shown to play a central role in the regulation of eukaryotic[15] and prokaryotic[16] gene expression via the modulation of messenger RNA (mRNA) stability and translation initiation.

In malaria parasites, poly-A addition does not necessarily occur at the eukaryotic canonical AAUAAA (SEQ ID NO: 1) site and poly-$A^-$ mRNA have been identified[17,18]. In the absence of an inducible system to genetically study essential malaria genes, the deletion of 3'UTR was used to decrease gene expression, revealing interpretable phenotypes[19,20]. To evaluate in vivo the contribution of the crucial merozoite subtilisin-like *P. berghei*-SUB2 protease[5,6] to the parasite life cycle, the inventors aimed to modulate Pbsub2 expression via the modification of its 3'UTR.

BRIEF DESCRIPTION OF THE INVENTION

The inventors have now demonstrated that efficient expression of the essential merozoite subtilisin-like maturase SUB2 strictly depends on functional poly-A sites, whose mutation gives rise to recombinant parasites over-expressing SUB2. The accumulation of SUB2 in these recombinant parasites correlates with more efficient maturation of the surface antigens MSP1 and AMA1, which are both vaccine candidates, and increased virulence of these recombinant *Plasmodium* organisms. The inventors thus show that non-coding regions involved in the regulation of crucial genes can be important virulence factors. Such genes may represent a dormant reservoir of virulence in *Plasmodium* and in other parasitic organisms in which invasion or virulence is mediated by enzymes involved in polypeptide/antigen maturation, such as the particular polypeptides/antigens which mediate host cell adhesion or invasion. Such parasitic organisms include *Toxoplasma, Babesia, Leishmania* and *Trypanosomes.*

For the first time, the inventors have now demonstrated that SUB2 is involved in the maturation of the merozoite surface vaccine candidates MSP1-42 and AMA1 and have shown that these maturations are not only crucial for the host cell invasion to succeed, but represent a limiting step on virulence in vivo. Based on these discoveries defining SUB2 as a maturase whose activity is critical for the biological cycle of malaria parasites, they establish that SUB2 is an anti-malaria drug target.

The inventors have discovered that the efficient expression of the essential merozoite subtilisin-like maturase *P. berghei*-SUB2[5,6] strictly depends on functional poly-A sites, the mutation of which gives rise to malaria parasites which over-express PbSUB2. A significantly higher parasite multiplication rate in vivo correlates with the accumulation of PbSUB2 since higher amounts of this enzyme provide a more efficient maturation of merozoite surface proteins, such as MSP1 (Merozoite Surface Protein 1) and AMA1 (Apical Merozoite Antigen 1), which are both candidate antigens for vaccine production.

Host cell invasiveness is known to be a key factor of malaria parasite virulence[1] which aggravates when the parasite does not show any selectivity for blood cells[3,23]. Beyond the first direct evidence that SUB2 is involved in the maturation of the merozoite surface vaccine-candidates MSP1-42 and AMA1, the present inventors genetically demonstrate that this maturation is not only crucial for the host cell invasion to succeed, thus confirming previous biochemical and immunological studies[21,24], but is also a limiting step in vivo. These discoveries indicate that in vivo, maturation of these proteins contributes to the invasion of host blood cells in an age-independent manner. The present inventors have thus defined SUB2 as a potent malaria virulence factor related to tropism independent host-cells invasion.

Based on these discoveries the present inventors describe new methods for determining and/or evaluating parasite virulence based on the presence of particular motifs in non-coding region sequences, such as a motif found in the 3' UTR of sub2. The 3' UTR or 3 prime untranslated region corresponds to a section of mRNA that is past the stop codon for a coding region or exon. Graphically it may be depicted as follows: 5'-----UTR translated RNA-----3'UTR.

Since regulation of sub2 gene expression has now been demonstrated to be an important virulence factor, methods of determining and/or evaluating and/or quantifying virulence may be based on the identification of regulatory sequences in the 3' UTR, the amount of sub2 mRNA (or cDNA corresponding to this mRNA), the amount of SUB2 protein expressed, or on SUB2 activity, for example, as measured by the post-translational processing of AMA1 or MSP1 polypeptides.

Increased or decreased virulence of a modified organism is based on a comparison with the virulence of corresponding unmodified organism or control strain. Likewise, the term “attenuated” means less virulent when compared to the corresponding unmodified or control strain.

A. Pbsub2 specific 3'RACE was performed on *P. berghei* segmented schizonts total RNA, fractionated on a 1.5% agarose gel, ethidium bromide stained (Lane 1) or Southern-blotted and probed with Sub2Cter (Lane 2). Lanes 3, 4 and 5 correspond to RT-PCR performed respectively without reverse transcriptase, on genomic DNA and without template. Size markers are indicated. Polyadenylation signals and CA addition sites of the Pbsub2 3' UTR are schematised on the left panel. The position of the nucleotides is relative to the Pbsub2 start codon.

B. Schematic representation of the wild type Pbsub2 3'UTR double crossing-over modification strategy and (bottom) the resulting WT-TmDX, single (SPA) or null poly-A sites (NPA) recombinant loci.

The polyadenylation sites (•), the TrimycDuoXpress™ (TmDX) epitope (hatched box) and the homologous coding (shaded) and untranslated (thickened) regions are indicated. The position of the BsmI (B), ClaI (C), HindIII (H) and Sad (S) restriction sites are indicated.

C. Genomic DNA prepared from WT-TmDX (w.) and SPA-TmDX (S.) cloned parasites was digested as indicated and probed with Sub2Cter or TgDhfr specific probes. The pattern obtained for SPA-TmDX gDNA supports a 0.2 kb truncation of the wild-type Pbsub2 3'UTR (FIG. 1C). Size markers are indicated.

FIG. 2: Comparative analysis of the Pbsub2 mRNA and protein in WT-TmDX1 and SPA-TmDX1 recombinant parasites.

A. Northern blot analyses were performed on total RNA extracted from wild type and recombinant parasites, fractionated and probed with Sub2Cter (upper panels) or Pbrab6 (lower panel) specific probes.

B. Western blot analysis of proteins SDS-extracted from segmented schizonts using anti-c-myc and trans-species specific anti-Plasmodium HSP70 specific monoclonal antibodies.

C. Subcellular localisation of the tagged PbSUB2 protein. Immunofluorescence analyses were performed on air-dried segmented schizonts, incubated with Sub2Cter-GST serum or the anti-c-myc plus the anti-Xpress™ monoclonal antibodies. Nucleus staining (Propidium Iodide, red) is merged with the antibody labelling (FITC, green).

FIG. 3: Comparative analysis of PbMSP1-42 and PbAMA1 maturation in WT-TmDX1 versus SPA-TmDX1 recombinant parasites.

Western blot analyses of SDS-extracted proteins from mature merozoites using rabbit anti-PbMSP1 polyclonal serum (arrows show PbMSP1 and PbMSP1-19 bands) (FIG. 3A), rat trans-species specific anti-AMA1/28G2 (arrows show PbAMA1 bands) (Fig. C) and mouse HSP70/1-C11 (Figs. B, D) specific monoclonal antibodies (arrows show PbHSP70 bands). The equivalent number of parasites per lane, and molecular weight markers are indicated.

Figure 4A:
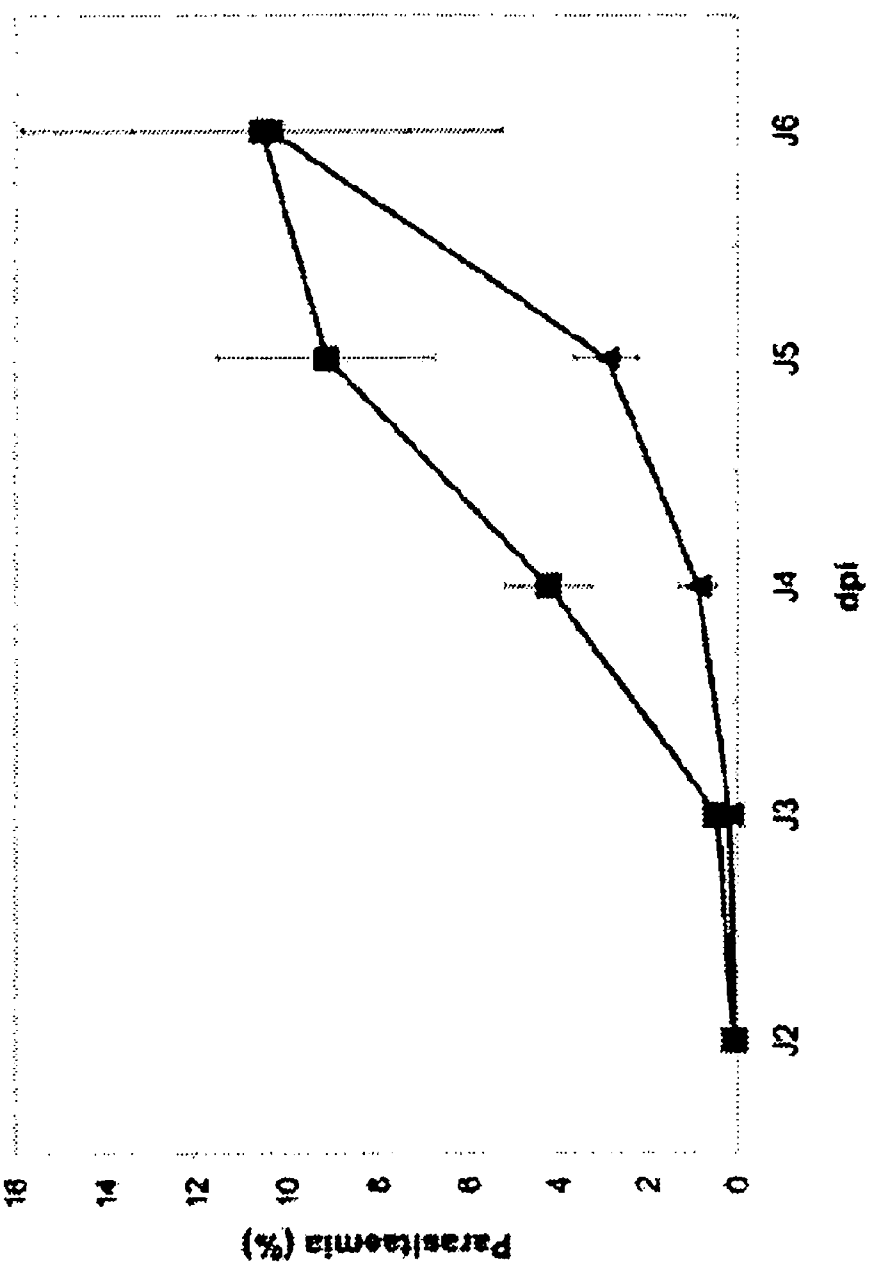
Figure 4B:
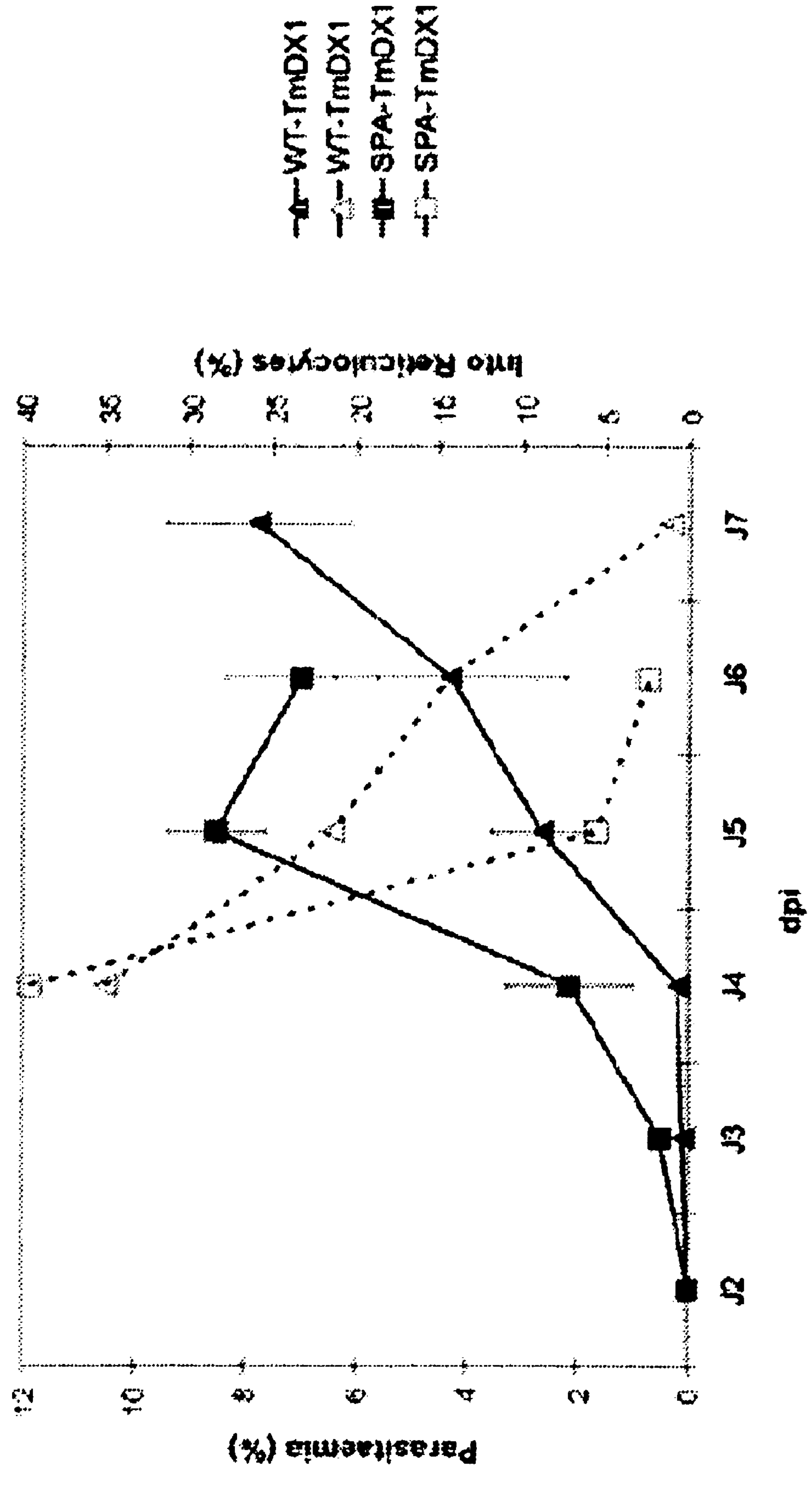

FIG. 4: In vivo multiplication rates of the WT-TmDX1 versus SPA-TmDX1 in Balb/c and C57Bl/6 mice.

Four BALB/cJ (A panel) or five C57Bl/6J mice (B panel) were infected with $5\times10^4$ WT-TmDX1 (triangle) or SPA-TmDX1 parasites (square). Parasitaemia monitored using Giemsa stained blood smears are presented from day 2 to day 6 post-injection (dpi). The percentage of WT-TmDX1 (open triangle) or SPA-TmDX1 (open square) parasites in reticulocytes is presented with broken lines on the right panel. Values represents mean±SD of 4-5 mice per group, $p<0.05$ versus WT-TmDX1 as calculated by Maim Whitney U-test.

Figure 5A:
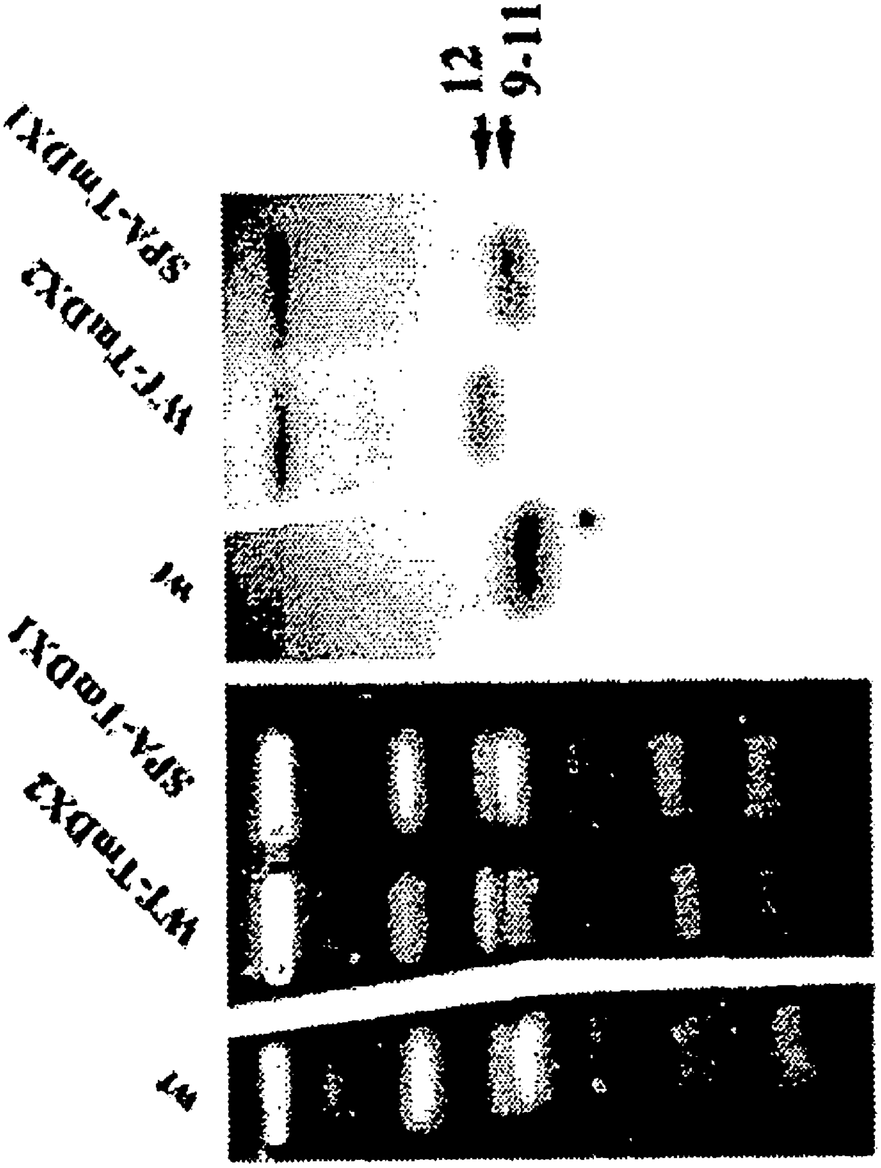
Figure 5B:
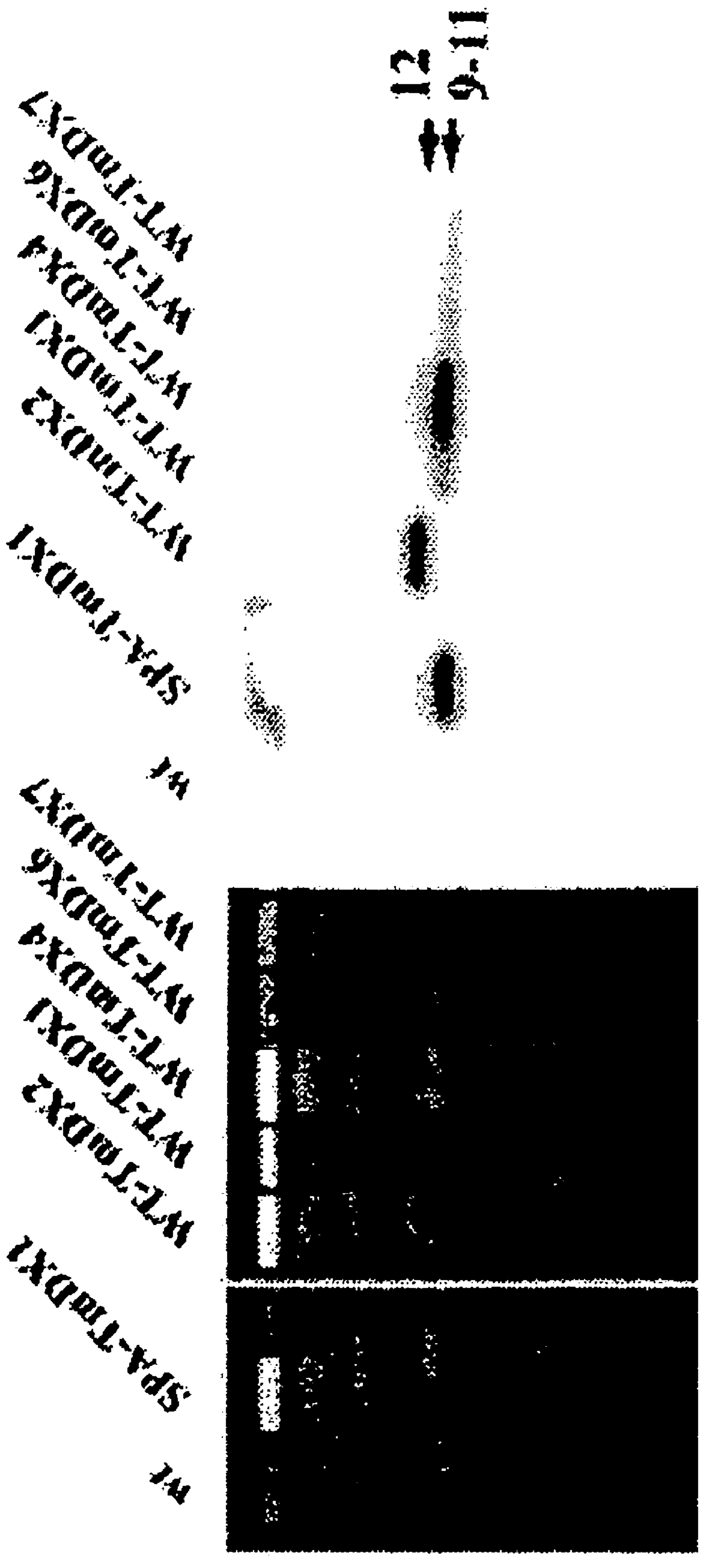

FIG. 5: Chromosomal localisation of the Pbsub2 recombinant loci.

The *P. berghei* chromosomes were prepared from wild type, SPA-TmDX and five WT-TmDX clones and separated by CHEF. Chromosomes 9 to 12 are indicated.

A. The wild type, WT-TmDX1 and SPA-TmDX1 *P. berghei* chromosomes were probed with Sub2Cter specific probe.

B. The wild type, SPA-TmDX1 and WT-TmDX1, 2, 4, 6 and 7 chromosomes were probed with TgDhfr specific probe. Given the unexpected rearrangement of the chromosome bearing Pbsub2 in the WT-TmDX2 clone, further analyses were performed with WT-TmDX1.

Figure 6:
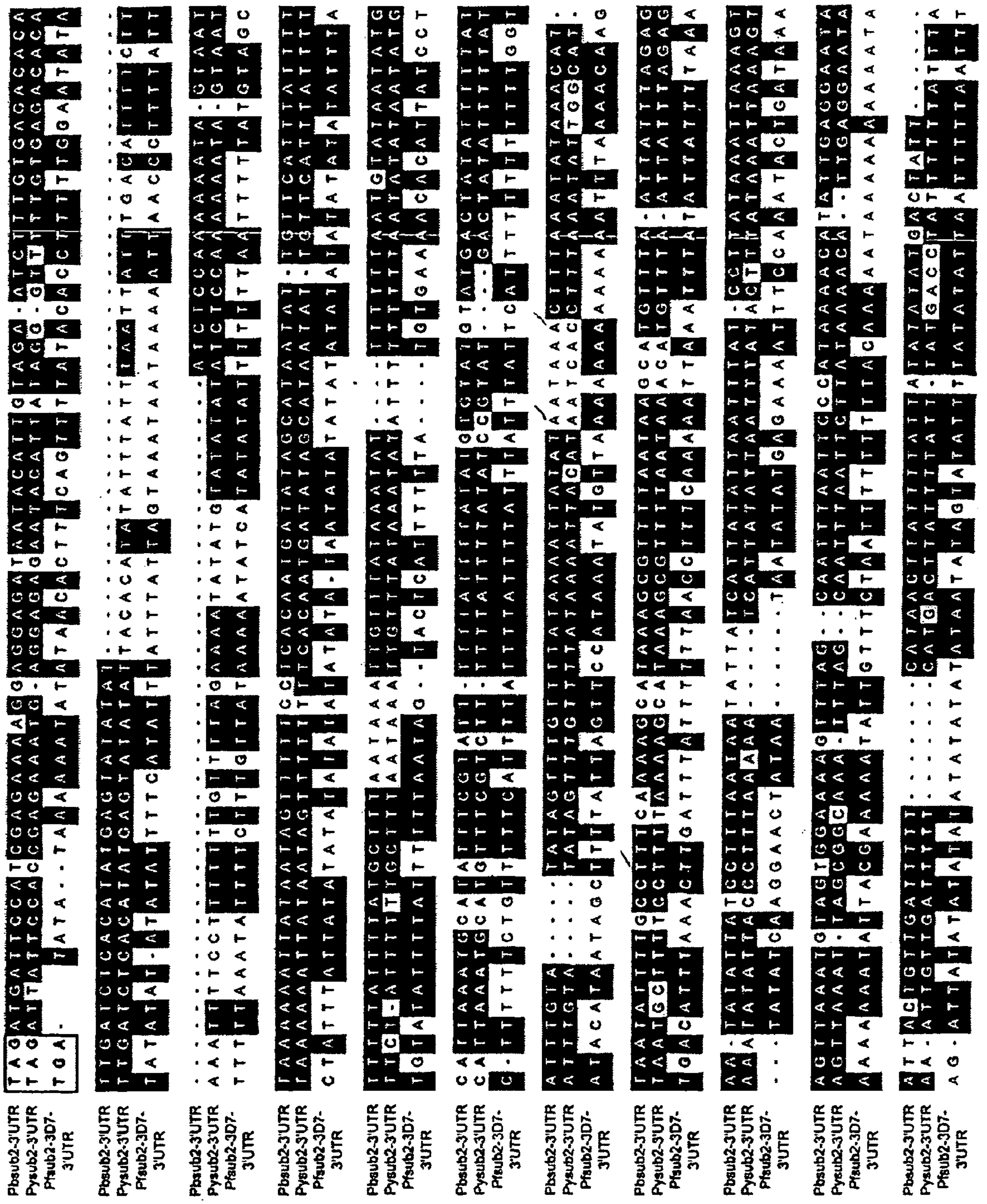

FIG. 6. Alignment of the 3'UTR of Pbsub2 (SEQ ID NO: 13), Pysub2 (SEQ ID NO: 14) and Pfsub2 (SEQ ID NO: 15).

The sequences corresponding to the 3'UTR of Pfsub2-3D7 and Pysub2, were extracted from the worldwide web at plasmodb.org, and aligned with Pbsub2 (Genebank access number AJ242629) using CLUSTALW (Thompson, J. D., Higgins, D. G. and Gibson, T. J. (1994). Nucleic Acids Research, 22:4673-4680). Identical residues appear in a black background and the stop codon of each gene is boxed.

"AAUAAA" (SEQ ID NO: 1) poly-adenylation signals and "CA" dinucleotides corresponding to the poly-A tail addition sites are labelled respectively in red and blue. Distal and proximal Pbsub2 "AAUAAA" (SEQ ID NO: 1) poly-adenylation signals described in this issue are indicated. Pfsub2 and Pysub2 putative "AAUAAA" (SEQ ID NO: 1) poly-adenylation signals and "CA" poly-A tail addition sites have been identified using online software available on the worldwide web at softberry.com/cgi-bin/programs/polyah.pl and rulai.cshl.org/sgi-bin/tools/polyadq.

Figure 7:
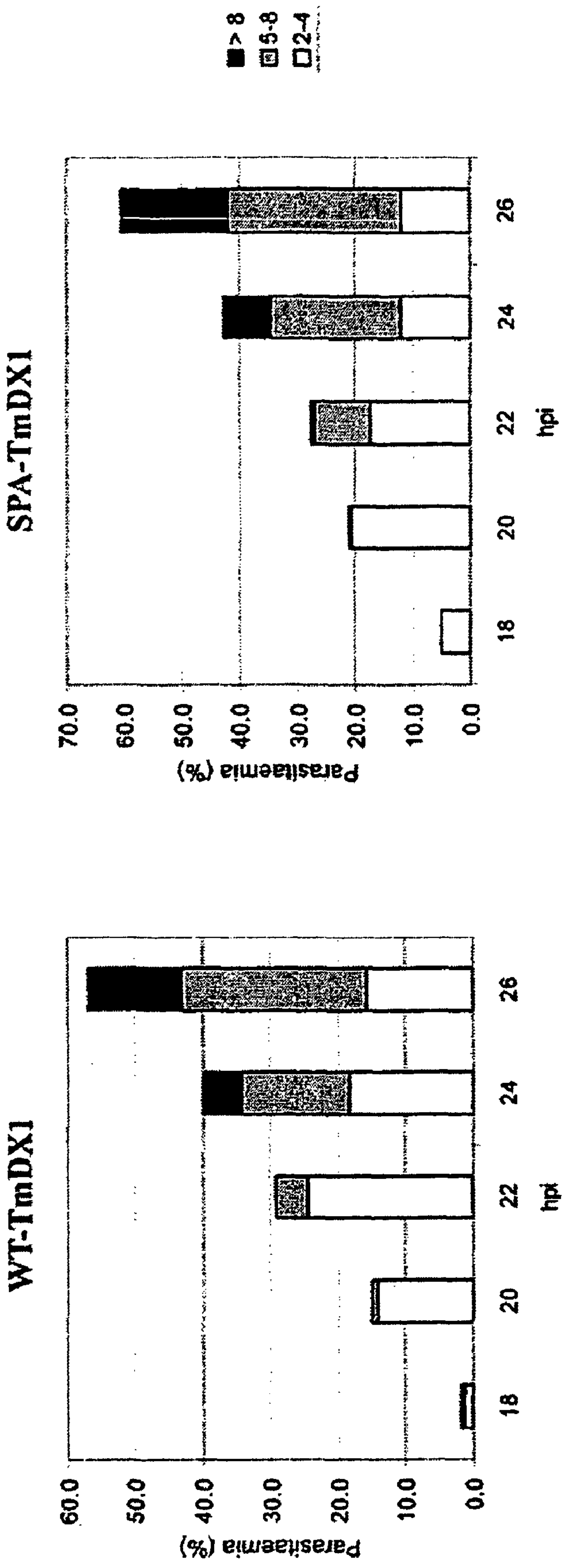

FIG. 7. Measure of the erythrocytic cycle length of WT-TmDX1 and SPA-TmDX1 parasites in vitro.

The WT-TmDX1 and SPA-TmDX1 parasites were synchronised by inoculation of mice with merozoites. The parasites collected 4 hours later were in vitro cultured for 26 hours post-invasion (hpi). The percentage of emerging parasites with 2 to 4 (plain line), 5 to 8 (broken line), and more than 8 nuclei (dots) has been determined every two hours from 18 to 26 hpi.

Determination of the in vitro schizogony properties. The synchronised WT-TmDX1 or SPA-TmDX1 parasites were prepared as follow: ten Swiss mice were infected with $2.5\times10^7$ parasites on day 0. Two days later, the blood was collected by heart puncture and maturated in vitro as previously described (van Dijk et al. (1995), *Science* 268, 1358-62). Merozoites were collected and injected into five Swiss mice. Four hours post-injection, the blood was collected and the parasites maturated in vitro for 18 to 26 hours. The parasites were counted according to their nuclei number using Giemsa stained blood smears.

DESCRIPTION OF THE PREFERRED EMBODIMENTS

Figure 1A:
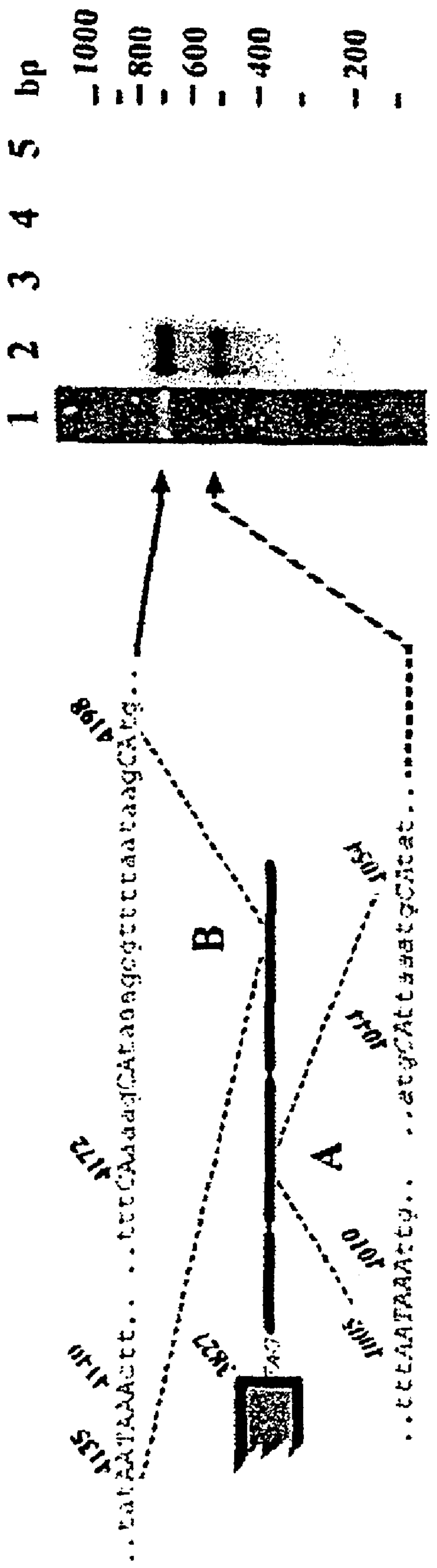
FIG. 1: Pbsub2 3'UTR characterization and modification following a double crossing-over strategy.

The 3'UTR of Pbsub2 was first characterised based on 3'RACE experiments using total RNA preparations from mature *P. berghei* schizonts (FIG. 1A). A major 750 bp and a weak 550 bp fragments hybridising to the Pbsub2 C-ter probe were amplified, consistent with the two predicted canonical polyadenylation motifs (AAUAAA) (SEQ ID NO: 1) (FIG. 1A, diagram). The sequence of six clones corresponding to the major 750 bp fragment revealed three different mRNA species with poly-A addition following CA dinucleotides 37, 43 and 62 bp respectively downstream from the distal and principally used AAUAAA (SEQ ID NO: 1) polyadenylation motif (FIG. 1A).

Figure 1B:
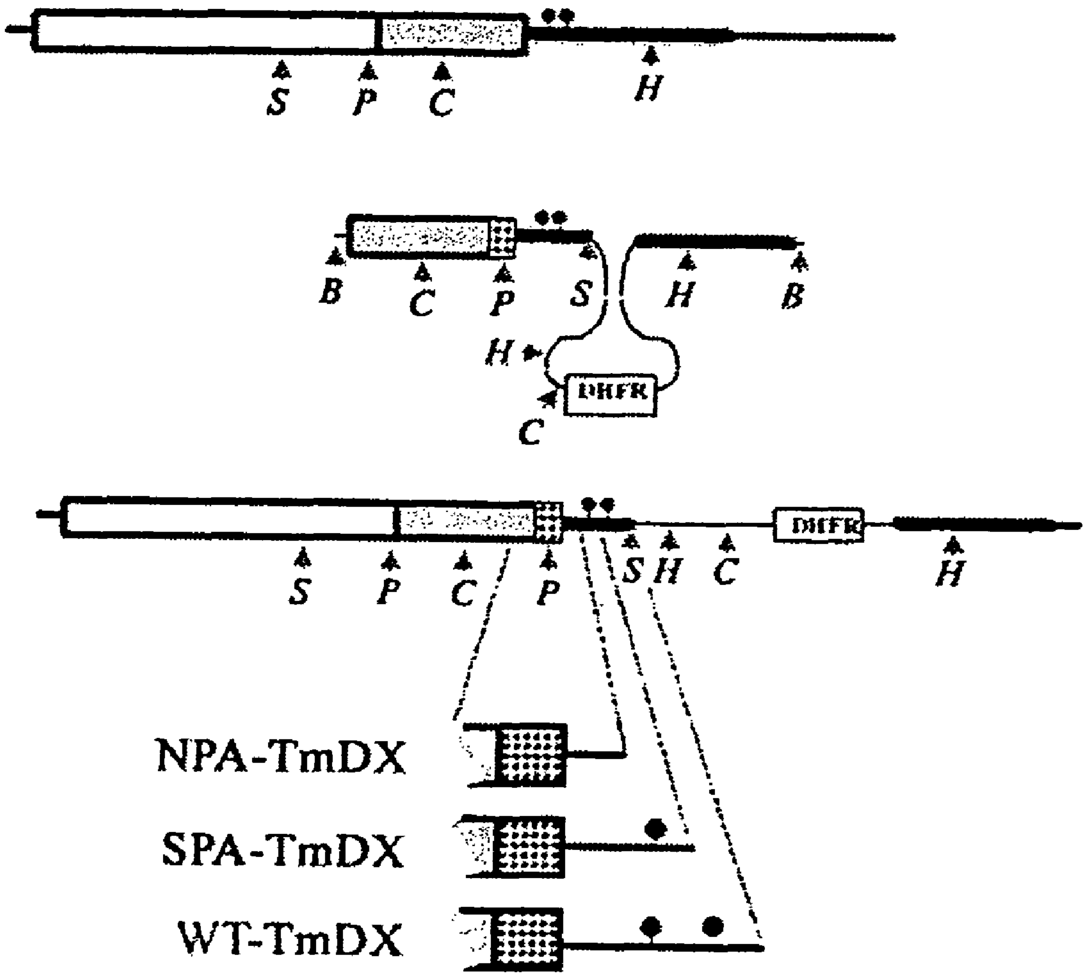
Figure 1C:
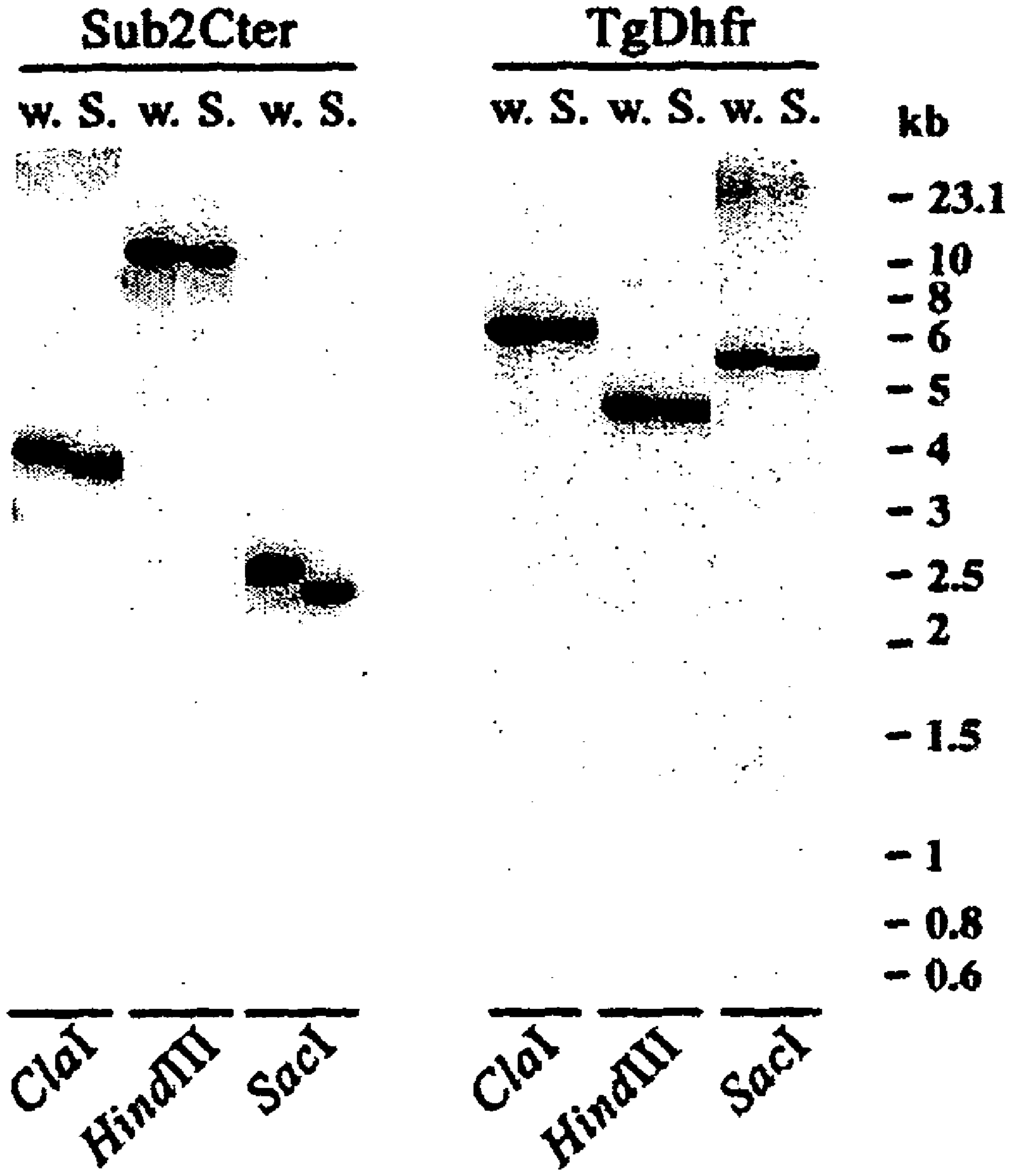

Two constructs were designed to sequentially delete Pbsub2 polyadenylation sites (FIG. 1B) following a double crossing-over event, giving rise respectively to the WT-TmDX[6], SPA-TmDX (Single PolyAdenylation site, corresponding to the proximal Pbsub2 polyadenylation site) and the NPA-TmDX (no polyadenylation site) recombinant parasites (FIG. 1B). Despite several attempts, the NPA-TmDX recombinant parasites were not recovered, while SPA-TmDX and WT-TmDX recombinant parasites were reproducibly selected using the same pool of parasites prepared for transfection experiments. The structure of the Pbsub2-locus from in vivo cloned recombinant parasites was assessed by Southern and chromosomal blots (FIG. 1C) and by PCR analyses.

The merozoite PbSUB2 protease being essential for the erythrocytic cycle, since, the inability to delete both Pbsub2 polyadenylation sites shows that the Pbsub2 transcript polyadenylation following canonical AAUAAA (SEQ ID NO: 1) sites is crucial for the correct expression of the PbSUB2 protease.

Plasmid pSPA from which *Plasmodium* SPA-TmDX can be obtained has been deposited at the CNCM on May 3, 2005 under accession number I-3423.

Interestingly, the 3'UTRs of *P. yoelii* and *P. falciparum* sub2 orthologs display similar polyA-addition motifs, (FIG. 6), suggesting a trans-species conserved post-transcriptional modification for the sub2 transcripts.

In eukaryotic cells, the use of canonical AAUAAA (SEQ ID NO: 1) and CA motifs to trigger polyadenylation involves a set of conserved proteins which form a complex after binding to the poly-addition motifs[15]. Data mining of the *P. yoelii* and *P. falciparum* genomes identifies putative orthologs of these proteins: a Poly-A Polymerase III (PAP), a Cleavage and Polyadenylation Stimulation Factor (CPSF), a Cleavage and Stimulation Factor (Cstf) and a Cleavage Factor I (CF1) that are respectively >33%, 50%, >30% and 30% identical to their eukaryotic counterparts (Table 1). While *P. falciparum* putative PAP mRNA expression is constitutive, the CPSF-like, Cstf-like and SUB2 mRNAs are concomitantly expressed during the merozoite biogenesis[5,6,9,10]. Therefore, although poly-A addition has previously been shown to occur at unusual sites[14,18], malaria parasites possess a classical stage regulated eukaryotic polyadenylation machinery which could be involved in post-transcriptional regulation of mRNA expression.

As suggested by the data in Table 1, the regulation of mRNA transcription or post-translational regulation of mRNA stability, as observed for the sub2 gene may also represent virulence factors for other *Plasmodium* proteins. Thus, alteration of mRNA transcription efficiency or mRNA stability for transcripts of these genes could affect virulence of *Plasmodium*. Many other bloodstream and intracellular parasites also encode enzymes involved in the maturation of antigens involved in attachment or invasion of host cells. Thus, a similar regulation of mRNA transcription or mRNA stability via sites in the 3'UTR of maturation enzymes in organisms such as Trypanosomes, *Leishmania, Babesia* and *Toxoplasma* may represent important virulence factors in these organisms as well. Therefore, the methods employing the *Plasmodium* sub2 gene, sub2 gene mRNA transcript, and SUB2 protein may also be applied to the genes and gene products from parasites other than *Plasmodium* in an analogous manner.

Figure 2A:
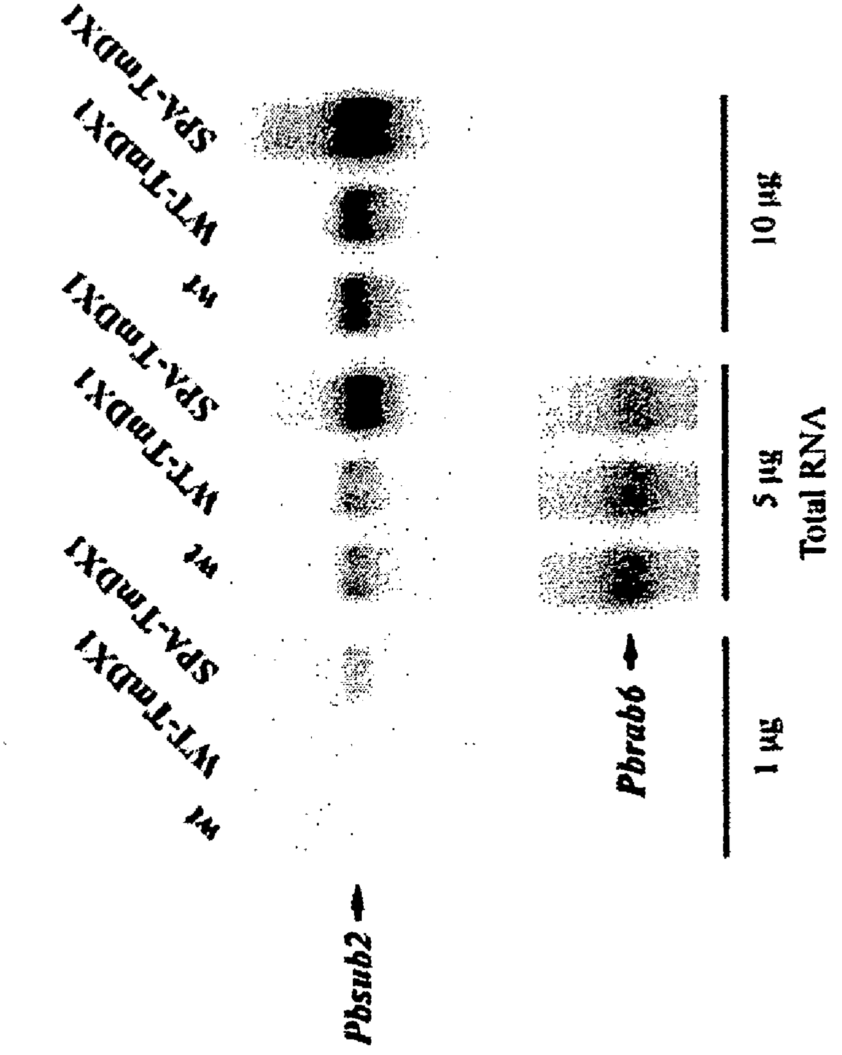
Figure 2B:
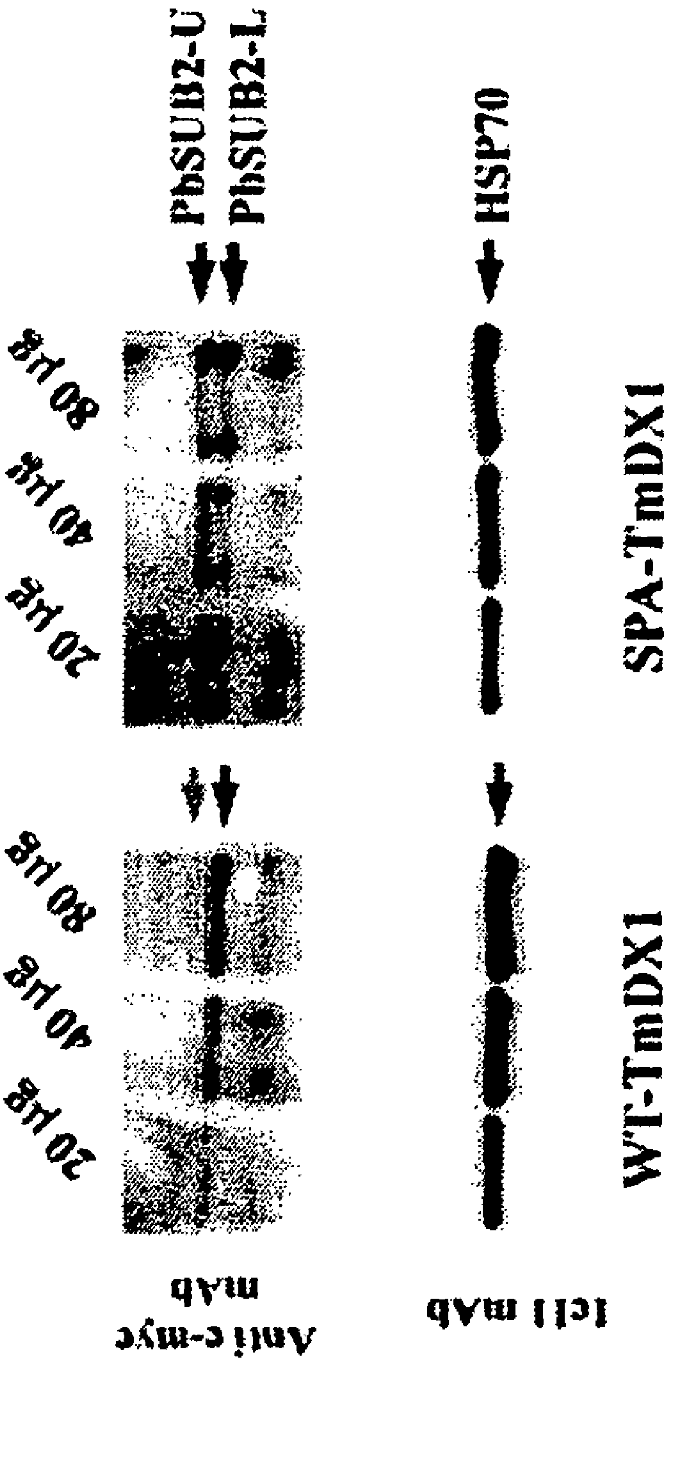
Figure 2C:
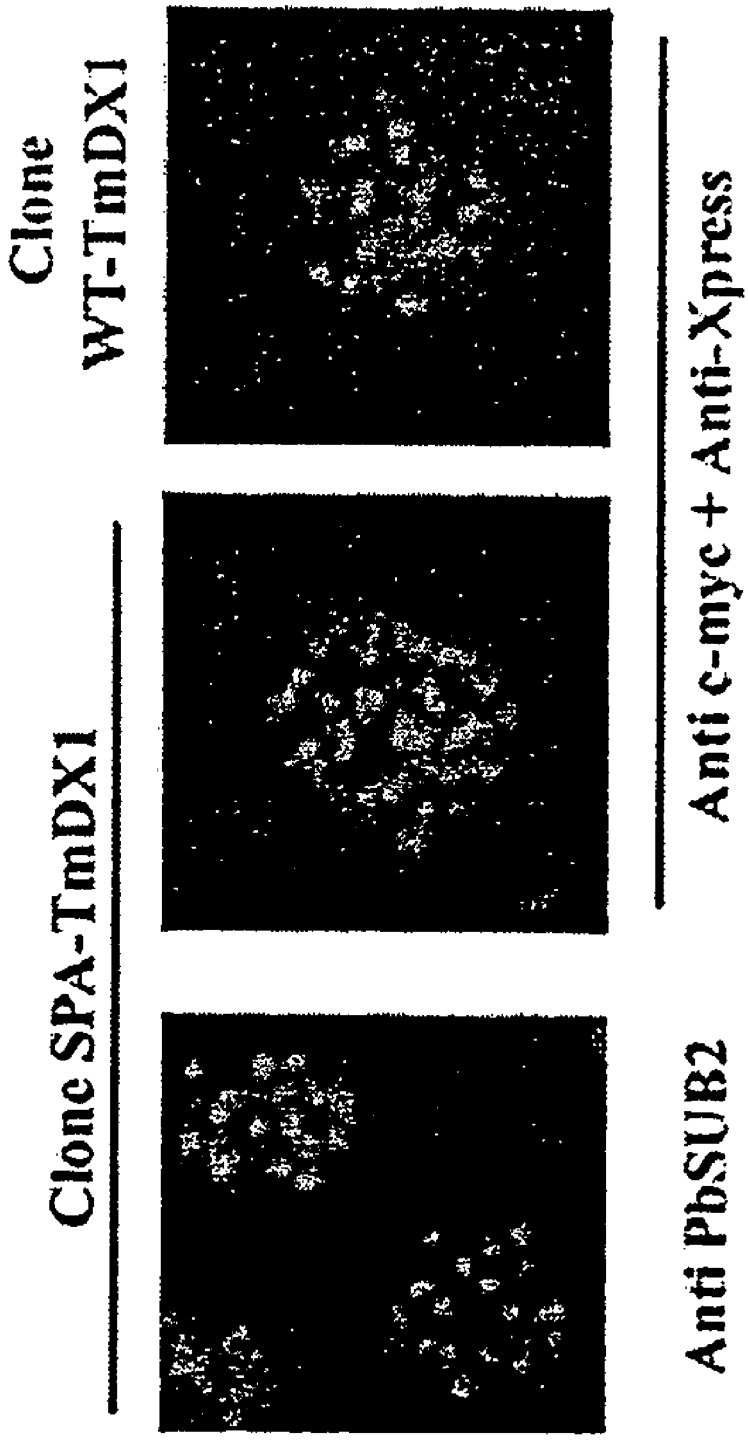
Figure 3A:
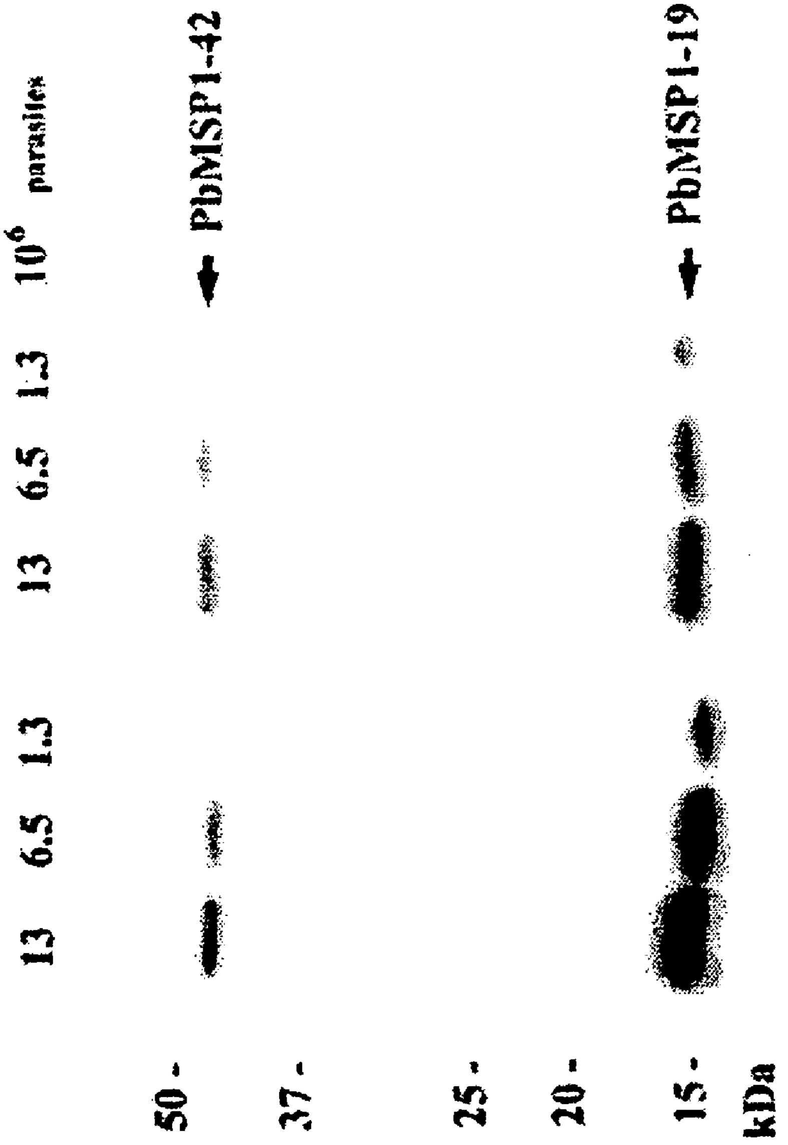
Figure 3B:
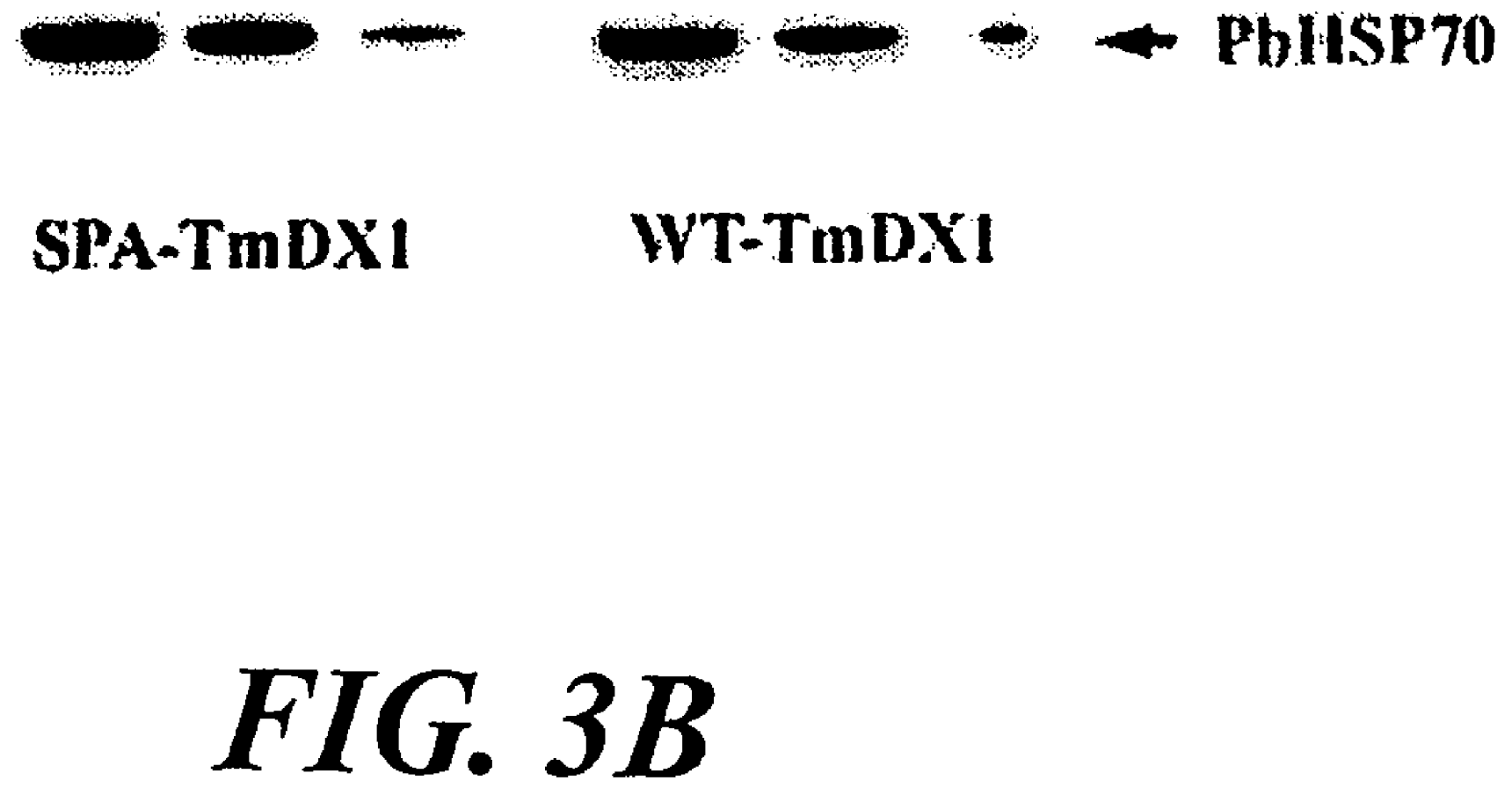
Figure 3C:
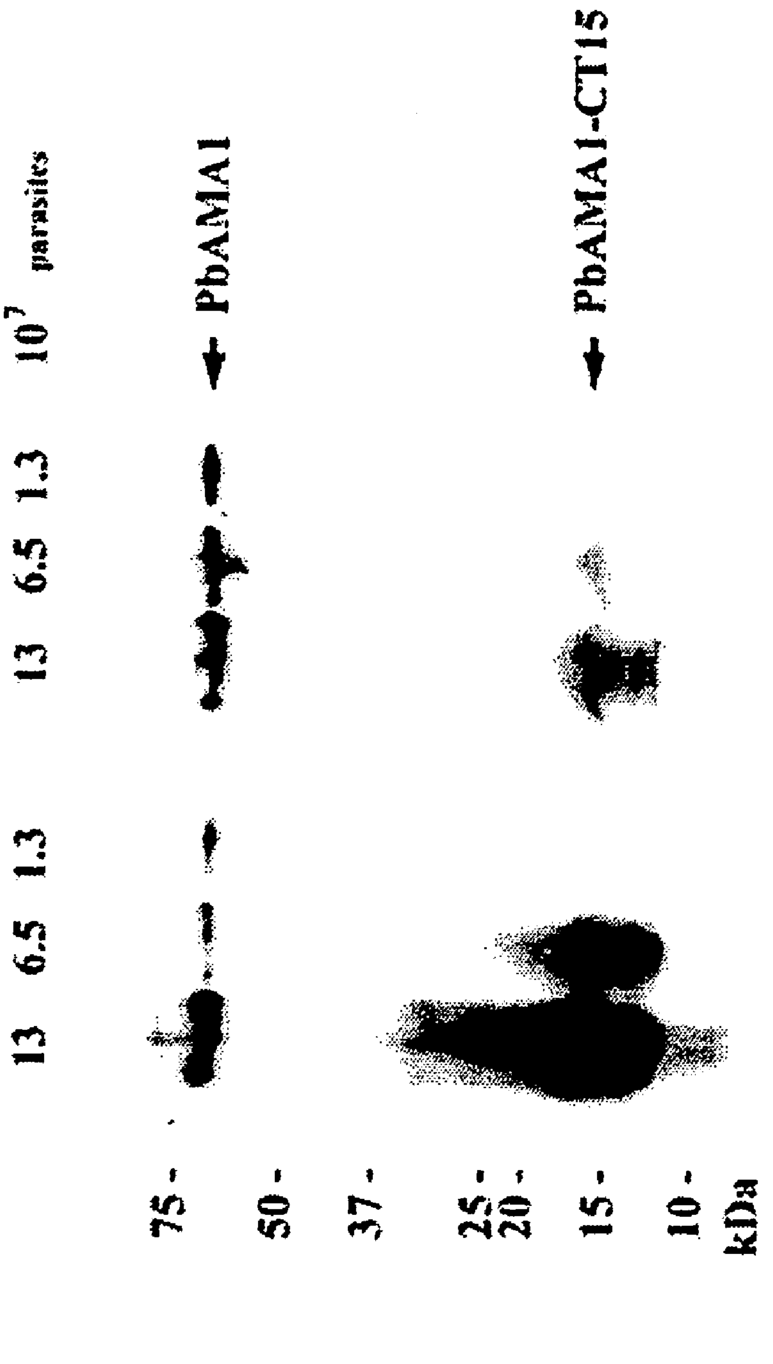
Figure 3D:

Quantitative Northern blot experiments revealed a 3 to 4 fold increase of the Pbsub2-mRNA in the SPA-TmDX1 clone compared to wild-type and WT-TmDX1 parasites (FIG. 2A and Table 2). Whether this phenotype is a consequence of a modified Pbsub2-mRNA transcription efficiency or stability is unknown, but it correlates with a two-fold increase of the recombinant SPA-TmDX1 PbSUB2-protein (FIG. 2B and Table 3). PbSUB2 protein principally accumulates as its intermediate activation form, whose final maturation takes place during its post-reticulum secretion[21]. Thus, the post-translational processing and localisation (FIG. 2C) of the SPA-TmDX1 PbSUB2-protein are identical to that found in wild-type parasites, indicating that the excess of PbSUB2 is available for further activation to perform its biological role.

To investigate the potential effects of PbSUB2 over-expression during the intra-erythrocytic parasite development, the inventors first compared the kinetics of schizogony by measuring the ratio of the 2-4, 4-8, and >8 nuclei during a comparative in vitro maturation of highly synchronised WT-TmDX1 and SPA-TmDX1 parasites (FIG. 7). Their timing of nuclei multiplication, average number of merozoites per schizont and erythrocytic cycle duration were not significantly different. This result is in accordance with the fact that PbSUB2 is a merozoite-specific enzyme which is not detectable in other parasite blood stages[5,6]. A contrario, when analysing in detail mature SPA-TmDX1 merozoites, it appears that the accumulation of PbSUB2 results in a significant increase of respectively the merozoite surface PbAMA1 15 kDa-C-terminal ((PbAMA1-CT15) and PbMSP1-19 maturation products (FIG. 3 & Tables 4 and 5).

The maturation of the merozoite surface MSP1-42 and the AMA1 has been shown to play a crucial role during the invasion process per se. The inventors have now determined that this observation which was obtained in vitro correlates with a virulence phenotype in vivo. As shown by the FIG. 4, SPA-TmDX1 parasites grow statistically faster in vivo than WT-TmDX1. This behaviour is independent from the host genetic background, since the injection of 5 $10^4$ parasites to Swiss (not shown), C57Bl/6J and BALB/cJ yields to respectively 84% and 46% increase of the multiplication rates in vivo for the PbSUB2 over-expressing SPA-TmDX1 parasites (FIG. 4 and Methods). The SPA-TmDX1 parasites increased growth rate in vivo leads to the death of the infected mice one day before the WT-TmDX1 infected ones. Thus, the 3'UTR-driven accumulation of PbSUB2 protein in SPA-TmDX1 parasites results in a significant increase of the parasite virulence in vivo.

The WT-TmDX1 and SPA-TmDX1 clones derive from *P. berghei* ANKA parasites, harbouring a marked tropism for reticulocytes[22]. Thus, the inventors investigated whether the multiplication rate difference between these clones was related to a better invasion of normocytes by SPA-TmDX1 parasites. At day 4 (2.5% parasitaemia), more than 30% of both WT-TmDX1 and SPA-TmDX1 parasites were detected in reticulocytes (FIG. 3B); when SPA-TmDX1 and WT-TmDX1 parasitaemia reached 8.5% and 7.8% on day 5 and 7 respectively, the proportion of parasites in reticulocytes decreased to 2.7% and 1.1% respectively. Based on these observations, PbSUB2 accumulation does not impair *P. berghei* tropism in vivo. The 2 day quicker consummation of reticulocytes being a consequence of the SPA-TmDX1 clone's higher multiplication rate in toto.

As a more general concern, the increase of *P. berghei* virulence in vivo following the modification of the Pbsub2 3'UTR indicates that malaria parasite virulence can be potentiated following the mutation of a single gene regulatory element. Preliminary results indicate that the *P. falciparum* Pfsub2 3'UTR is highly polymorphic and could lead to *Plasmodium falciparum* parasites over-expressing PfSUB2. Adaptation of parasite gene expression to a selective pressure has been shown to participate in the resistance to anti-malarials[20,25]. Thus, non-coding regions involved in the regulation of expression of crucial *Plasmodium* genes should now be considered as potential virulence factors, a situation already reported for some viruses and bacteria[26-28].

This large latent reservoir of virulence may not yet have been explored by the parasite but could be revealed under a sub-lethal selective pressure, such as a partial immunity driven by vaccines which reduces pathogen growth rate[29,30]. Since the selection of such vaccine overcoming parasites is not anticipated in clinical trials, and considering the large population targeted, this observation may lead to dramatic consequences for public health following imperfect intervention strategies against malaria parasites, or other invasive pathogens. Malaria pathogens include those which infect humans, simians and other animals, for example, *Plasmodium berghei, Plasmodium brasilianum, Plasmodium chabaudi, Plasmodium cynomolgi, Plasmodium falciparum, Plasmodium gallinaceum, Plasmodium knowlesi, Plasmodium lophurae, Plasmodium malariae, Plasmodium ovale, Plasmodium reichenowi* and *Plasmodium vivax.*

The following sequences are incorporated by reference. *P. falciparum* SUB2 (AJ132006 and NC_004315, geneID: 810927) (SEQ ID NO: 11); *P. yoelii* SUB2 (PY01222, proteinID: EAA20512.1) (SEQ ID NO: 12); *Toxoplasma gondii* SUB2 and SUB1 (AF420596 and AY043483, respectively). Detailed information about the structures and functions of 3'UTR is incorporated by reference to Proudfoot et al., Curr. Biol. 12:R855-7 (2002).

A recombinant *Plasmodium* according to the invention may comprise a modified regulatory segment within the 3'UTR. Such a modification may increase or decrease the expression of a gene like sub2, which encodes a protein involved in maturation or post-translational processing of other parasite antigens, such as the SUB2 subtilisin-like maturase. Recombinant organisms having modifications in the 3'UTR which provide higher amounts of a maturase like SUB2 have been demonstrated to be more virulent compared to the corresponding unmodified strains. Similarly, recombinant strains modified to express less of a maturase like SUB2 (e.g., an attenuated strain) would be expected to be less virulent. An example of a use for a less virulent strain would be as a live vaccine or as a comparative control. More virulent strains can be used in vaccine testing procedures, for example, to test the efficacy of a particular vaccine, to provoke particular humoral or cellular immune responses, or as comparative controls in assays involving *Plasmodium* strains with other virulence characteristics.

To detect or evaluate the virulence of a *Plasmodium* strain, the amount of SUB2 protein expressed by that strain compared to a control strain may be determined. Alternatively, the amount of sub2 mRNA may be detected or measured as a comparative indication of virulence of the test and control strains. Methods for determining the levels a particular protein, such as SUB2, are well known in the art, for example, SUB2 levels may be determined by ELISA or Western blotting using antiserum to SUB2 epitopes. The mRNA encoding SUB2 may also be determined or quantified by conventional methods.

Methods for determining the amount of mRNA (or corresponding cDNA) encoding a *Plasmodium* protein such as SUB2, AMA1 or MSP-1 are well known in the art and are also incorporated by reference to *Current Protocols in Molecular Biology*, Chapter 25 (2005) which is incorporated by reference.

Western blotting and other methods of identifying or quantitating the amounts of a particular protein, such as SUB2, AMA1 or MSP-1 are well known in the art and are also incorporated by reference to *Current Protocols in Molecular Biology*, e.g. Chapters 10 and 11 (2005) which is incorporated by reference.

For some applications, proteins that are essentially identical or at least 90%, 95%, or 99% similar to SUB2, AMA1 or MSP-1 may be used to construct a recombinant *Plasmodium* according to the present invention. Generally, a nucleic acid sequence encoding a variant will have 70%, preferably 80%, more preferably 90, 95 or 99% similarity to a native sequence. Such similarity may be determined by an algorithm, such as those described by *Current Protocols in Molecular Biology*, vol. 4, chapter 19 (1987-2005) or by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Likewise, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Coding sequences for these proteins may also be determined by the ability of a polynucleotide to hybridize under stringent conditions to the complement of a coding region of a known SUB2, AMA1 or MSP-1 gene. Such hybridization conditions may comprise hybridization at 5×SSC at a temperature of about 50° C. to 68° C. Washing may be performed using 2×SSC and optionally followed by washing using 0.5×SSC. For even higher stringency, the hybridization temperature may be raised to 68° C. or washing may be performed in a salt solution of 0.1×SSC. Other conventional hybridization procedures and conditions may also be used as described by *Current Protocols in Molecular Biology,* (1987-2005), see e.g. Chapter 2.

The polynucleotide of the invention which comprises a *Plasmodium* subtilisin-like maturase SUB2 untranslated region and a regulatory segment differs from the corresponding native sequence. The difference may be in the deletion or addition of a regulatory segment, such as a polyadenylation site, or in the polynucleotide sequence of a regulatory segment.

The deletion, addition or alteration of the regulatory segment provides a different degree of SUB2 protein expression (it modulates protein expression) than that of the corresponding native sequence. The polynucleotide may be conveniently isolated or purified from other nucleic acids or components of *Plasmodium*. The alteration in the regulatory sequence of the 3'UTR may occur within a polyadenylation site. Such a regulatory segment or polyadenylation site may conform to the native motif, but have 1, 2, 3, 4, 5 or more nucleotides deleted, inserted or substituted compared to the native sequence. Preferably, an altered regulatory segment will contain a high degree of similarity to the native sequence, e.g. 60, 70, 80, 90, 95% similarity, but will function to increase or decrease SUB2 expression compared to the native sequence. Such increases may range from 1, 2, 5, 10, 20, 50, 100, 200% or more compared to the level of expression of SUB2 provided by the unmodified native sequence. Similarly, a modified regulatory sequence may decrease SUB2 expression down to 95, 90, 80, 75% 50, 40, 25, 10, 5% or less of SUB2 expression provided by the unmodified native regulatory sequence. The same parameters apply to regulatory sequences for other non-SUB2 genes involved in antigen or polypeptide processing in *Plasmodium* or other parasites.

Polyadenylation sites or other motifs in a 3'UTR may be identified using software such as CLUSTALW. Sequences and/or motifs shared by the 3'UTRs of *Plasmodium* species are also graphically described by FIG. 6.

High-throughput screening of candidate molecules is known in the art. U.S. Pat. No. 6,770,451 describes a method for screening enzyme inhibitors, U.S. Pat. No. 6,368,789 describes a method for identifying telomerase inhibitors and U.S. Pat. No. 6,051,373 describes methods for screening inhibitors of the transcription-enhancing activity of the X protein of hepatitis B virus. The screening methods and libraries disclosed by these patents is incorporated by reference. None of these documents disclose the use of the SUB2 target molecule of the present invention. Comb. Chem. High Throughput Screen. 2005 February; 8(1)(see entire volume) also describes a number of different methods and libraries for high throughput screening of anti-malaria agents. These methods and libraries are also incorporated by reference. Large numbers of test compounds may be efficiently screened for their ability to bind and/or inhibit SUB2 activity. These test compounds may have various structures, such as small organic molecules having a molecular mass of about 50 to 2,500 daltons, molecules containing metal ions, carbohydrates, saccharides, peptides having less than 100 residues, polypeptides, antibodies, and molecules or other products isolated from natural sources such as from bacteria, fungi, parasites, plants, and animals.

EXAMPLES

Methods

Parasites. *P. berghei* parasites were amplified and collected as previously described[6]. Noteworthily, due to the reactivity of the anti-c-myc-specific monoclonal antibody (mAb) with the host 30 kDa Myc proteins, special care was taken to deplete leucocytes using Plasmodipur™ filters (Euro-Diagnostica, the Netherlands), before preparing erythrocyte extracts for Western blotting experiments.

Polyadenylation sites mapping. RT-PCR analyses were performed with 1 μg of total RNA as previously described[6]. The 3' untranslated region of Pbsub2 was reverse transcribed from 1 μg of total segmented-schizont RNA using the Tun primer ($^{5'}$TTTTTTTTTTTTTTTTTTTT[ACG][ACGT]$^{3'}$) (SEQ ID NO: 5). The resulting cDNA was PCR amplified using the Tun and CterBamHI ($^{5'}$TTGGATCCCATCATCAAAGTAAACAACGCG$^{3'}$) (SEQ ID NO: 6) primers (95° C., 20 sec; 45° C., 1 min, 62° C., 2 min for 3 cycles; then 95° C., 20 sec; 50° C., 1 min; 62° C., 2 min for 30 cycles), separated in 1% agarose gels, cloned into the pCR2.1-TOPO vector (Invitrogen), and sequenced using a Sequenase 2 kit (USB corporation).

Generation of transfected constructs. The pSub2-SPA-TmDX and pSub2-NPA-TmDX plasmids were obtained following the same three step procedure used for the pSub2-WT-PA plasmid, with the following modifications[6]. The Pbsub2-

3'UTR fragments used to generate the pSub2-SPA-TmDX and pSub2-NPA-TmDX plasmids were PCR amplified with the reverse primers $^{5'}$CCGGATCCATAAAAATATAGTCATACATAC$^{3'}$ (SEQ ID NO: 7) and $^{5'}$CCGGATCCATATTATGCTATATCATTGTGA$^{3'}$ (SEQ ID NO: 8) respectively. The constructs were entirely sequenced prior to transfection.

Parasite transfection and nucleic acids analyses. Seventy micrograms of each BsmI digested plasmid DNA were transfected into purified schizonts of the *P. berghei* ANKA strain and pyrimethamine selection of the transformed parasites were performed as previously described[6]. The pSub2-SPA-TmDX transfected parasites were cloned by limiting dilution as previously described[6]. Southern and Northern blot analyses were performed as described with the appropriate probe[6]. The Rab6 probe was PCR amplified using the $^{5'}$TGGGAGAACAAGCAGTTGG$^{3'}$ (SEQ ID NO: 9) and $^{5'}$GTAACCTTTCTAAGATCGGCC$^{3'}$ (SEQ ID NO: 10) primers, and dATP[$\alpha^{32}$P] labelled (Megaprime™, AP Biotech). The Northern blot bands were quantified using the Quantity One® software (Biorad).

Immunodetection. For PbSUB2 quantification, total proteins were extracted from WT-TmDX1 and SPA-TmDX1 parasites using 2% SDS and quantified following the Folin method (Sigma) prior to gel loading. Western blot analyses were performed as described[6] using 1:5000 diluted horseradish peroxidase (HRP) coupled c-myc mAb or 1:5000 diluted 1c11 mAb, revealed with HRP coupled secondary antibodies. The 1c11 and c-myc mAb labelling was detected using SuperSignal Pico™ and SuperSignal Femto™ reagents respectively (Pierce). The bands were quantified using the Quantity One® software (Biorad).

Immunofluorescence assays were performed on air-dried thin films of *P. berghei* infected erythrocytes using 1:50 diluted Sub2Cter-GST sera or 1:100 diluted anti-c-myc and anti-Xpress mAb as previously described[6]. Primary antibodies were revealed using Alexa Fluor® Green anti-mouse antibodies (Molecular Probes).

In vivo infection of mice and determination of the average daily multiplication rate.

The average daily multiplication rate (ADMR) was calculated as:

$$ADMR=\{[Parasitaemia\times(1\times10^{10})]/(5\times10^{4})\}^{1/4}$$

where $1\times10^{10}$ and $5\times10^{4}$ stand respectively for the erythrocyte total number per mouse and the total number of parasites injected at day 0. The ADMR values obtained are 9.5 and 8.1 for SPA-TmDX1 and 6.5 and 4.4 for WT-TmDX1 parasites in BALB/cJ and C57Bl/6J mice respectively.

Table 1: Description of the putative parasite orthologs involved in the polyadenylation addition. Data were extracted from plasmodb.org on the worldwide web (Bahl, et al, (2003). PlasmoDB: the *Plasmodium* genome resource. A database integrating experimental and computational data. *Nucleic acid research,* 31, 212-215.

SUPPLEMENTAL TABLE 1

Description of the putative parasite orthologs involved in the polyadenylation addition. Data were extracted from www.plasmodb.org. (Bahl et al, (2003). PlasmoDB: the *Plasmodium* genome resource. A database integrating experimental and computational data. Nucleic acid research, 31, 212-2 15)

| Abbreviation | Name | PlasmoDB access number | Chomosome location | Minimum % of identity with eukaryotic putative orthologues |
|---|---|---|---|---|
| CPSF | Cleavage and Polyadenylation Stimulation factor | PFC0825w PY00757 | PFC0825w: 3 | 50% of identity with eukaryotic putative orthologues |
| Cstf | Cleavage Stimulation factor | PFI1600w PY02603 | PFI1600w: 9 | 30% of identity with eukaryotic putative orthologues |
| PAP | PolyA Polymerase III | PFF1240w PY02044 | PFF1240w: 6 | 33-40% of identity with eukaryotic putative orthologues |
| CF1 | Cleavage Factor I | PFA0450c | PFA0450c: 1 | 30% of identity with *A. thaliana* CF1 |

Table 2: Quantification of the Pbsub2 mRNA in wild-type, WT-TmDX1 and SPA-TmDX1 parasites. The amounts of mRNA are presented in arbitrary units. The ratios of SPA-TmDX1 over wild type and WT-TmDX1 intensity counts are presented (nd: not determined).

| | Wild Type | | | WT-TmDX1 | | | SPA-TmDX1 | | |
|---|---|---|---|---|---|---|---|---|---|
| | 1 μg | 5 μg | 10 μg | 1 μg | 5 μg | 10 μg | 1 μg | 5 μg | 10 μg |
| Pbsub2 mRNA | nd | 138 | 347 | nd | 128 | 373 | 47 | 541 | 1011 |
| $\frac{\text{SPA-TmDX1 value}}{x}$ Ratio | | 3.9 | 2.9 | | 4.2 | 2.7 | | | |

Table 3: Quantification of the PbSUB2 protein from WT-TmDX1 and SPA-TmDX1 extracts.

The amounts of PbSUB2 and PbHSP70 proteins are presented in arbitrary units. The ratio between PbSUB2 and HSP70 corresponding to the corrected amount of PbSUB2 is presented (1). The ratio between PbSUB2 corrected amounts from WT-TmDX1 and SPA-TmDX1 protein extracts are presented in bold (2).

| | WT-TmDX1 | | | SPA-TmDX1 | | |
|---|---|---|---|---|---|---|
| | 20 µg | 40 µg | 80 µg | 20 µg | 40 µg | 80 µg |
| PbSUB2 | 115 | 253 | 516 | 238 | 457 | 627 |
| HSP70 | 2623 | 3372 | 3935 | 2315 | 2863 | 3372 |
| PbSUB2/HSP70 Ratio (1) | 0.044 | 0.075 | 0.131 | 0.103 | 0.160 | 0.186 |
| WT-TmDX1 Ratio (1) / SPA-TmDX1 Ratio (1) Ratio (2) | | | | **2.3** | **2.1** | **1.4** |

Table 4: Quantification of the AMA1 protein from WT-TmDX1 and SPA-TmDX1 extracts.

The amounts of PbAMA1-CT15 and PbHSP70 proteins are presented in arbitrary units. The ratio between PbAMA1-CT15 and PbHSP70 corresponding to the corrected amount of PbAMA1 is presented (1). The ratio between PbAMA1-CT15 corrected amounts from WT-TmDX1 and SPA-TmDX1 protein extracts is presented in bold (2).

| | WT-TmDX1 | | SPA-TmDX1 | |
|---|---|---|---|---|
| Parasites | $6.5 \times 10^7$ | $13 \times 10^7$ | $6.5 \times 10^7$ | $13 \times 10^7$ |
| PbAMA1-CT15 | 104 | 606 | 1140 | Out of range |
| HSP70 | 668 | 1017 | 751 | 1603 |
| PbAMA1-CT15/HSP70 Ratio (1) | 0.16 | 0.60 | 1.52 | / |
| SPA-TmDX1 Ratio (1) / WT-TmDX1 Ratio (1) Ratio (2) | | | **9.7** | / |

Table 5: Quantification of the PbMSP1-19 protein from WT-TmDX1 and SPA-TmDX1 extracts.

The amounts of PbMSP1-19 and PbHSP70 proteins are presented in arbitrary units. The ratio between PbMSP1-19 and PbHSP70 corresponding to the corrected amount of PbMSP1-19 is presented (1). The ratio between PbMSP1-19 corrected amounts from WT-TmDX1 and SPA-TmDX1 protein extracts are presented in bold (2). Underlined values correspond to under-estimated ratios due to the saturation of the signal on the film.

| | SPA-TmDX1 | | | WT-TmDX1 | | |
|---|---|---|---|---|---|---|
| Parasites | $13 \times 10^6$ | $6.5 \times 10^6$ | $1.3 \times 10^6$ | $13 \times 10^6$ | $6.5 \times 10^6$ | $1.3 \times 10^6$ |
| PbMSP1-19 | 7380 | 5189 | 1599 | 3725 | 1911 | 464 |
| HSP70 | 2541 | 2079 | 796 | 2636 | 1892 | 664 |
| PbMSP1-19/HSP70 Ratio (1) | 2.90 | 2.50 | 2.01 | 1.41 | 1.01 | 0.70 |
| SPA-TmDX1 Ratio (1) / WT-TmDX1 Ratio (1) Ratio (2) | | | | 2.1 | 2.5 | **2.9** |

Modifications and Other Embodiments

Various modifications and variations of the described products and methods and their methods of use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Modifications of the described modes of the invention which would be obvious to those skilled in the microbiological, parasitological, molecular biological, diagnostic, therapeutic, pharmacological and biochemical arts or related fields are intended to be within the scope of the following claims.

CITATIONS

1. Mackinnon, M. J. & Read, A. F. Virulence in malaria: an evolutionary viewpoint. *Philos Trans R Soc Lond B Biol Sci* 359, 965-86 (2004).
2. Breman, J. G., Alilio, M. S. & Mills, A. Conquering the intolerable burden of malaria: what's new, what's needed: a summary. *Am J Trop Med Hyg* 71, 1-15 (2004).
3. Chotivanich, K. et al. Parasite multiplication potential and the severity of falciparum malaria. *J Infect Dis* 181, 1206-9 (2000).
4. Rasti, N., Wahlgren, M. & Chen, Q. Molecular aspects of malaria pathogenesis. FEMS Immunol Med Microbiol 41, 9-26 (2004).
5. Barale, J. C. et al. *Plasmodium falciparum* subtilisin-like protease 2, a merozoite candidate for the merozoite surface protein 1-42 maturase. *Proc Natl Acad Sci USA* 96, 6445-50 (1999).
6. Uzureau, P., Barale, J. C., Janse, C. J., Waters, A. P. & Breton, C. B. Gene targeting demonstrates that the *Plasmodium berghei* subtilisin PbSUB2 is essential for red cell invasion and reveals spontaneous genetic recombination events. *Cell Microbiol* 6, 65-78 (2004).
7. de Koning-Ward, T. F., Janse, C. J. & Waters, A. P. The development of genetic tools for dissecting the biology of malaria parasites. *Annu Rev Microbiol* 54, 157-85 (2000).

8. Gardner, M. J. et al. Genome sequence of the human malaria parasite *Plasmodium falciparum*. *Nature* 419, 498-511 (2002).
9. Bozdech, Z. et al. The transcriptome of the intraerythrocytic developmental cycle of *Plasmodium falciparum*. *PLoS Biol* 1, E5 (2003).
10. Le Roch, K. G. et al. Global analysis of transcript and protein levels across the *Plasmodium falciparum* life cycle. *Genome Res* 14, 2308-18 (2004).
11. Horrocks, P., Dechering, K. & Lanzer, M. Control of gene expression in *Plasmodium falciparum*. *Mol Biochem Parasitol* 95, 171-81 (1998).
12. Militello, K. T., Dodge, M., Bethke, L. & Wirth, D. F. Identification of regulatory elements in the *Plasmodium falciparum* genome. *Mol Biochem Parasitol* 134, 75-88 (2004).
13. Corredor, V. et al. A SICAvar switching event in *Plasmodium knowlesi* is associated with the DNA rearrangement of conserved 3' non-coding sequences. *Mol Biochem Parasitol* 138, 37-49 (2004).
14. Golightly, L. M., Mbacham, W., Daily, J. & Wirth, D. F. 3' UTR elements enhance expression of Pgs28, an ookinete protein of *Plasmodium gallinaceum*. *Mol Biochem Parasitol* 105, 61-70 (2000).
15. Proudfoot, N. & O'Sullivan, J. Polyadenylation: a tail of two complexes. *Curr Biol* 12, R855-7 (2002).
16. Jasiecki, J. & Wegrzyn, G. Growth-rate dependent RNA polyadenylation in *Escherichia coli*. *EMBO Rep* 4, 172-7 (2003).
17. Levitt, A., Dimayuga, F. O. & Ruvolo, V. R. Analysis of malarial transcripts using cDNA-directed polymerase chain reaction. *J Parasitol* 79, 653-62 (1993).
18. Ruvolo, V., Altszuler, R. & Levitt, A. The transcript encoding the circumsporozoite antigen of *Plasmodium berghei* utilizes heterogeneous polyadenylation sites. *Mol Biochem Parasitol* 57, 137-50 (1993).
19. Thathy, V. et al. Levels of circumsporozoite protein in the *Plasmodium* oocyst determine sporozoite morphology. *Embo J* 21, 1586-96 (2002).
20. Waller, K. L. et al. Chloroquine resistance modulated in vitro by expression levels of the *Plasmodium falciparum* chloroquine resistance transporter. *J Biol Chem* 278, 33593-601 (2003).
21. Blackman, M. J. Proteases in host cell invasion by the malaria parasite. *Cell Microbiol* 6, 893-903 (2004).
22. Deharo, E., Coquelin, F., Chabaud, A. G. & Landau, I. The erythrocytic schizogony of two synchronized strains of *Plasmodium berghei*, NK65 and ANKA, in normocytes and reticulocytes. *Parasitol Res* 82, 178-82 (1996).
23. Simpson, J. A., Silamut, K., Chotivanich, K., Pukrittayakamee, S. & White, N. J. Red cell selectivity in malaria: a study of multiple-infected erythrocytes. *Trans R Soc Trop Med Hyg* 93, 165-8 (1999).
24. Dutta, S., Haynes, J. D., Moch, J. K., Barbosa, A. & Lanar, D. E. Invasion-inhibitory antibodies inhibit proteolytic processing of apical membrane antigen 1 of *Plasmodium falciparum* merozoites. *Proc Natl Acad Sci USA* 100, 12295-300 (2003).
25. Myrick, A., Munasinghe, A., Patankar, S. & Wirth, D. F. Mapping of the *Plasmodium falciparum* multidrug resistance gene 5'-upstream region, and evidence of induction of transcript levels by antimalarial drugs in chloroquine sensitive parasites. *Mol Microbiol* 49, 671-83 (2003).
26. Edgil, D., Diamond, M. S., Holden, K. L., Paranjape, S. M. & Harris, E. Translation efficiency determines differences in cellular infection among dengue virus type 2 strains. *Virology* 317, 275-90 (2003).
27. Mangold, M. et al. Synthesis of group A streptococcal virulence factors is controlled by a regulatory RNA molecule. *Mol Microbiol* 53, 1515-27 (2004).
28. Stoecklin, G., Gross, B., Ming, X. F. & Moroni, C. A novel mechanism of tumor suppression by destabilizing AU-rich growth factor mRNA. *Oncogene* 22, 3554-61 (2003).
29. Gandon, S., Mackinnon, M. J., Nee, S. & Read, A. F. Imperfect vaccines and the evolution of pathogen virulence. *Nature* 414, 751-6 (2001).
30. Mackinnon, M. J. & Read, A. F. Immunity promotes virulence evolution in a malaria model. *PLoS Biol* 2, E230 (2004).

What is claimed is:

1. A method for identifying a compound that decreases the virulence of a *Plasmodium* parasite comprising:

contacting an isolated *Plasmodium* SUB2 (subtilisin-like maturase) protein with a test compound and a substrate of SUB2 selected from the group consisting of *Plasmodium* AMA1 (Apical Membrane Antigen-1) and MSP1 (Merozoite Surface Protein 1), determining the activity of *Plasmodium* SUB2 on the substrate in the absence and in the presence of the test compound, selecting a test compound which decreases the activity of SUB2 on the substrate, and evaluating the effect on *Plasmodium* virulence of the selected test compound in vivo, thus identifying a compound that decreases *Plasmodium* parasite virulence in vivo.

2. The method of claim 1, wherein the test compound is a chemical molecule, a peptide, a pseudopeptide, or an antibody.

3. The method of claim 1, wherein measuring activity of *Plasmodium* SUB2 is determined using a fluorescent method or Western blotting.

4. The method of claim 1, wherein the activity of *Plasmodium* SUB2 on its substrate is determined by measuring the rate at which the substrate degrades.

5. The method of claim 1, wherein a fluorogenic peptide with the sequence of MSP1 (Merozoite Surface Protein 1) is used as the substrate.

6. The method of claim 1, wherein a fluorogenic peptide with the sequence of AMA1 (Apical Membrane Antigen-1) is used as the substrate.

7. A method for identifying a compound decreasing the virulence of a *Plasmodium* parasite comprising contacting a cell expressing *Plasmodium* SUB2 with a test compound in the presence of a substrate selected from the group consisting of *Plasmodium* AMA1 and *Plasmodium* MSP1 , determining the activity of SUB2 on the substrate compared to an otherwise identical control cell not exposed to said test compound; and identifying a compound decreasing the virulence of a *Plasmodium* parasite by selecting a compound decreasing the activity of SUB2 compared to the activity of SUB2 in the control cell.

8. A method for identifying a compound decreasing the virulence of a *Plasmodium* parasite comprising:

contacting a cell expressing *Plasmodium* SUB2 mRNA with a test compound, determining the amount of SUB2-encoding mRNA, comparing said amount of SUB2-encoding mRNA to the amount of SUB2-encoding mRNA of an otherwise identical control cell not exposed to said test compound, and identifying a compound decreasing the virulence of a *Plasmodium* parasite by selecting a drug decreasing the amount of SUB2-encoding mRNA compared to the control cell.

9. The method of claim 1, wherein the identified compound decreases MSP-1 maturation.

10. The method of claim 1, wherein the identified compound decreases AMA1 maturation.

11. The method of claim 1, wherein said *Plasmodium* SUB2 protein is from *Plasmodium berghei, Plasmodium falciparum* or *Plasmodium yoelii.*

12. The method of claim 1, wherein said *Plasmodium* SUB2 protein has a sequence that has at least 95% similarity to the sequence of a polypeptide encoded by SEQ ID NO: 11 or 12.

13. The method of claim 1, which consists essentially of:

contacting an isolated *Plasmodium* SUB2 (subtilisin-like maturase) protein with a test compound and a substrate of *Plasmodium* SUB2 that is *Plasmodium* AMA1 (Apical Membrane Antigen-1), determining the activity of SUB2 on the substrate in the absence and in the presence of the test compound, selecting a test compound which decreases the activity of SUB2 on the substrate, and evaluating the effect on *Plasmodium* virulence of the selected test compound in vivo, thus identifying a compound that decreases *Plasmodium* parasite virulence in vivo.

14. The method of claim 1, which consists essentially of:

contacting an isolated *Plasmodium* SUB2 (subtilisin-like maturase) protein with a test compound and a substrate of *Plasmodium* SUB2 that is *Plasmodium* MSP1 (Merozoite Surface Protein 1), determining the activity of SUB2 on the substrate in the absence and in the presence of the test compound, selecting a test compound which decreases the activity of SUB2 on the substrate, and evaluating the effect on *Plasmodium* virulence of the selected test compound in vivo, thus identifying a compound that decreases *Plasmodium* parasite virulence in vivo.

15. A method for identifying a compound that attenuates the virulence of a *Plasmodium* parasite by reducing the activity of *Plasmodium* SUB2 in a *Plasmodium* parasite comprising:

contacting an isolated *Plasmodium* SUB2 (subtilisin-like maturase) protein with a test compound and a substrate of SUB2 selected from the group consisting of *Plasmodium* AMA1 (Apical Membrane Antigen-1) and MSP1 (Merozoite Surface Protein 1), determining the activity of *Plasmodium* SUB2 on the substrate in the absence and in the presence of the test compound, selecting a test compound which decreases the activity of SUB2 on the substrate, thus identifying a compound that attenuates *Plasmodium* parasite virulence compared to a *Plasmodium* parasite not contacted with the test compound.

16. The method of claim 15, further comprising evaluating a test compound that decreases the activity of SUB2 on the substrate for its ability to decrease the virulence of *Plasmodium* in a subject infected with *Plasmodium.*

* * * * *

SEQUENCE LISTING

<160> NUMBER OF SEQ ID NOS: 15

<210> SEQ ID NO 1
<211> LENGTH: 6
<212> TYPE: RNA
<213> ORGANISM: artificial
<220> FEATURE:
<221> NAME/KEY: misc_feature
<223> OTHER INFORMATION: Eukaryotic canonical site

<400> SEQUENCE: 1 aauaaa 6

<210> SEQ ID NO 2
<211> LENGTH: 552
<212> TYPE: DNA
<213> ORGANISM: Plasmodium berghei
<220> FEATURE:
<221> NAME/KEY: misc_feature
<223> OTHER INFORMATION: sub2 3' UTR

<400> SEQUENCE: 2

```
tagatgattc catcgagaaa aggaggagat aatacattgt agaatctttg tgagacacat     60
tgatctcaca tatgagtata tatatctcca aaaaatagta attaaaaaat tataatagtt    120
tttcctcaca atgatatagc ataatattgt tcatttattt ttttttattt tatgctttaa    180
taaattgttt ataaatattt ttttaatgta taatatgcat taaatgcata tttcgtattt    240
tttattttat atgtgtatgt atgactatat ttttatattt gtatatagtt tgttttataa    300
aattatataa taaactttaa atataaacat taatattttg cctttcaaaa gcataaagcg    360
ttttaataag catgtttaat tatttagaga atatattatc ctttaataat attatcatta    420
tattaattta tccttataaa ttaaagtagt taaatgtagt ggaaaagttt agcaatttaa    480
ttcccataaa acatattgag gaataattac tgttgatttt tcataactta ttttattata    540
tatatgacta tt                                                        552
```

<210> SEQ ID NO 3
<211> LENGTH: 858
<212> TYPE: DNA
<213> ORGANISM: Plasmodium yoelii
<220> FEATURE:
<221> NAME/KEY: misc_feature
<223> OTHER INFORMATION: sub2 3' UTR

<400> SEQUENCE: 3

```
tagattattc caccgagaaa tgaggagaga atacattata gggtttttgt gagacacatt     60
gatctcacat atgagtatat attacacata tatttattta attatttgac attttcttaa    120
attttccttt ttttgtttta gaaaatatat gtatatatat ctccaaaaaa tagtaattaa    180
aaaattataa tagttttttt tcacaatgat atagcataat attgttcatt tatttttttct    240
attttttgct ttaataaatt gtttataaat atattttttt ttaatatata atatgcatta    300
aatgcatgtt tcgtcttttt tattttatat ccgtatgact atatttttat atttgtatat    360
agtttgtttt ataaaattac ataatcacct ttaaatattg gcattaatgc ttttcctttt    420
aaaagcataa agcgttttaa taaacatgtt taattattta gagaaatata ttacccttta    480
aaaatcatta tattaattta tactttataa attaaagtag ttaaattagc ggcaaattta    540
gcaatttaat tcttataaaa cattgaggaa taaaattgtt gatttttcat gacttatttt    600
atttatgacc tattttttat ttagtatgta ataaatacac ttttataccc tcaaataaaa    660
ttttcttaca atttatttta tttatatatt tgtggaaaag aaaaatttaa cattaaaaaa    720
aatatatacg ctataaaaac tttataaata ttatttttga ataaatattt tattaaaagc    780
caaaaaataa aaaatatatc tataaaaaaa agccagataa aaattttatt aattagctaa    840
ttttttttt atcacaaa                                                    858
```

<210> SEQ ID NO 4
<211> LENGTH: 850
<212> TYPE: DNA
<213> ORGANISM: Plasmodium falciparum
<220> FEATURE:
<221> NAME/KEY: misc_feature
<223> OTHER INFORMATION: Strain 3D7, sub2 3' UTR

<400> SEQUENCE: 4

```
tgatatataa aaaatatata acactttcag ttttatacac ctttttggaa tatatatata     60
tatatatttt catatttatt tattagtaaa taataaaaat taacccttt atttttttaa    120
atattttctt tgttataaaa atatcatata tatttttta atttttatgt agcctattta    180
```

-continued

```
ttatatatat atatatatat ataatatata tatatatata tatatatatt tatgtatatt    240

ttatttttta atagtactca tttttatgt gaaaacacat tatcctcttt tttctgtttt    300

tcattttatt ttattttatt tatttattca tttttttttt ttggtataca taatagcttt    360

tattagttcc ataaatatgt taaaaaaaaa aaaatttaaa acaagtgaca tttaaacttg    420

atttattttt taacctttca aaaattaaat ttatattatt ttaaatatat caaggaacta    480

taataatata tgagaaaatt tccaaatact gataaaaaaa aaatattacg aaaaatattg    540

tttctaattt ttttttacaa aaataaaaaa aaaataagat tatatatata tatatatata    600

taatatagta tattttatat attaattttt aatttctatt aaataaagat atatattata    660

actatataat tatataagat atatatattt atattttaat aaaaataaat attaaataaa    720

atatcttctt aaagttaata ttatatatat atgattttat atataattat ttacataatt    780

attattatcg agttttatat ttaatttatg ttaagataaa aaaaaaaaaa aaaatatata    840

taacttttta                                                            850
```

<210> SEQ ID NO 5
<211> LENGTH: 27
<212> TYPE: DNA
<213> ORGANISM: artificial
<220> FEATURE:
<223> OTHER INFORMATION: Tun primer

<400> SEQUENCE: 5

```
tttttttttt tttttttttt acgacgt    27
```

<210> SEQ ID NO 6
<211> LENGTH: 31
<212> TYPE: DNA
<213> ORGANISM: artificial
<220> FEATURE:
<223> OTHER INFORMATION: primer

<400> SEQUENCE: 6

```
tttggatccc atcatcaaag taaacaacgc g    31
```

<210> SEQ ID NO 7
<211> LENGTH: 30
<212> TYPE: DNA
<213> ORGANISM: artificial
<220> FEATURE:
<223> OTHER INFORMATION: reverse primer

<400> SEQUENCE: 7

```
ccggatccat aaaaatatag tcatacatac    30
```

<210> SEQ ID NO 8
<211> LENGTH: 30
<212> TYPE: DNA
<213> ORGANISM: artificial
<220> FEATURE:
<223> OTHER INFORMATION: reverse primer

<400> SEQUENCE: 8

```
ccggatccat attatgctat atcattgtga    30
```

<210> SEQ ID NO 9
<211> LENGTH: 20
<212> TYPE: DNA
<213> ORGANISM: artificial
<220> FEATURE:
<223> OTHER INFORMATION: primer -continued

<400> SEQUENCE: 9
ttgggagaac aagcagttgg 20

<210> SEQ ID NO 10
<211> LENGTH: 21
<212> TYPE: DNA
<213> ORGANISM: artificial
<220> FEATURE:
<223> OTHER INFORMATION: primer

<400> SEQUENCE: 10
gtaacctttc taagatcggc c 21

<210> SEQ ID NO 11
<211> LENGTH: 4611
<212> TYPE: DNA
<213> ORGANISM: Plasmodium falciparum

<400> SEQUENCE: 11
cacgaggtct cgagtttttt tttttttttt ttgttatttt tttttttctc tttccgtata 60
atgctgaata ttatttatgt ggtttccttg atattaataa aatttatctt ttataaggaa 120
tgtaataata ataataataa ttatttaagt aatatagaat tatataatta taaactaagg 180
aagagaaaca ggattctaaa taataatata aatgatagga aatccttttt gtctgattta 240
gaacaaaatt acaaaccatt atttgacata tatgagttat cagctaattt tgagaaaaga 300
agaaaagagt tagagaaaaa aacaaaggga gaagaaaatg aaatagaaaa aaaaaaggaa 360
aatgatttag aaaaaaaaaa agaaaatgat ttagaaaaag aatataatga tgtcataaat 420
ttattagaat taagtttaag ttctgaatat aaggaactaa atgccgatgt aagtaataat 480
gataattctg gacatgagga aaataataaa cacaaattaa ataaaaaaaa ttcttcaaat 540
tataaaaatg ataaatctct tgatgaatta attaaaggcg caatacttaa attgaaacag 600
aatccaaata taaaaaataa aaatatgttg gattatgata aaatatttaa aataattaaa 660
gaaaaattaa tcaataagaa tttggctagt aacaaaataa ggggggggtga taatgaaaaa 720 ttaaaagagg aaaaaaaaca aagcgatata tcaacaaatg tagaagtcaa aaaagatatc 780
ataaatgatc aactaaataa aggtatacct acaaagaaag aaaataaaga tgatatgata 840
aataaagaaa gtaataagga ggatattact aatgaaggaa aatcgaattc tcttaataat 900
ttgaatacat taaataatga tggaaacata ataacaaaag tatatgacca ctatactata 960
gtaaccaatt ctaacgatat attaaatgat atttctattg atgcctcaga tatatcaaaa 1020
aatagtatag gaggtattaa tataccttttt aatgaaaacg ataatagtag ttttactcat 1080
cagagatata tagtactatc aaacaatgga gaaaaaaaat acaaaatagt tttaatgaca 1140
aagaatccta aatttatgga tatggatggt atatatgatg aagaagaaaa aaaagaatct 1200
cttattgaat taaatcaaaa ggtaaacaag gaggaaaata caaacctttta tgatggaacg 1260 gggacattat attatggtaa aaaatccaaa aaggaaaaag aaaatacaca acaaaaagga 1320
ggaaataatc caaatgtaga cataaacata ctcaacaata ataataataa taataataat 1380
aataacaata ataataatag taataataat agtaatagta tgaatgacga agaaatcaat 1440
tataataata ataataataa taaagaatca ccaagtatgt tcagacgttt tataaacttt 1500
ttaagtttct caggtaatga aaatgaaaca gaagatactt taatttatca taataaaaat 1560
gataattcct acaaaaataa aaaagaagga actggtaaaa ataatgataa taatgatcct 1620
aataataata ataataaaaa aattttgtta aatgttgata aacttgtaga tcaatatcta 1680

-continued

```
ttaaacttaa aaaataatca cacatcgaaa caggaattga tacttgtact taaaggagaa   1740
ttagatcttc attcgaaaaa tatgaaaaat gttacaaata atgcaaagaa aaatttagaa   1800
aaatatttta aagaacactt taaggaattc gataaaatat catatgatat atcaacaccc   1860
attaattttc tttgtatttt tataccaact gtttttgata tgaataatat ggatttactt   1920
aaacaagcac tattaatatt acatagtgat ctacacgaat atgttgaaaa ttggagtttt   1980
tctagtacat accatacata cgaagcggat tatataaagg aacaagattc tgtgtatgat   2040
agatctccaa agaaaaaata tataaaagcg agtaaaaaat tatataacaa caaatattct   2100
tttttaaata aattcttaaa tattgaacca cttatattat ttgctaaaaa gttaaattca   2160
aaacgttcaa atattgagaa agaaatttta aattttttac ctaaggaatt aagagattat   2220
tccacatgga atttgtcaat tattagagtg ttcaatgcgt ggtttctggc tggatatggg   2280
aataagaatg taaaggtatg tgttgttgat tcaggggcag atataaatcg tgttgattta   2340
aatggtaatt tatatatacc agaatataat gaaaaatatg aaatgactca agatttttat   2400
aacttcatgg ttaaaaaatc ctacagatgc ttaggtcatg gatcacatgt cactggtatt   2460
ataggaggtg tagctaatga tttaggtgta gtaggtgtag ctcctaatat tacattaata   2520
tcattaagat ttattgatgg aaaaaaatat ggtggaagtt ttcatgctat taaggcttta   2580
aatgtatgta tattaaataa agcaccaatt ataaatgcta gttggggctc tagtcatttt   2640
gacgttaatt tacatctgac tgtggagaga ttaaaatata cattaaatgg aaaggggagt   2700
gtgttaatag cagcatccgg aaataaaagt aacgataatg atatttcacc tttataccct   2760
gcaacattta catttcctca tgtttatagg taatacagaa tatgtataaa atatatgcaa   2820
gttggaaatg aattaatatg tatatatgga tatatatatg tatatatatg tatatatata   2880
tatatgttta ttttttttat tttttatttt ttatttttat tctttttttgt agtgtggcct   2940
ccattagcag aaattttgaa atttctccgt tctcaaatta tggatataag agtgtgcaca   3000
ttttagcccc aggtcatcac atatattcta ctattccaaa taactcatac aagatcttta   3060
caggtacttc tatggctgct cctcatgtat gtggtgtgag tgctttggta tattccgttt   3120
gttataacca aggttttatt cctcaagcgg aagaggtgtt agatatatta acaaggacat   3180
ctataaaaat aatttctaca aagaaaagaa ccataaatga cagtttagtt aatgcagaag   3240
gagcagtttt gactacttta ttaggaggac tatggatgca aatggattgt tattttgtta   3300
aatttaattt agaaaaaggc aagaaaaagc atattcctgt tgttttctcg gcttacaaga   3360
aaggagtata tgaaacagat atcgttatag ctattatacc tattgatggg aaatccaaaa   3420
tatatggaga aattcatatt cctataaaaa ttgtaaccga tgtaaatatt cccaatttcc   3480
aagaatctcc acgaagagga aaaaattata ctatagattc taatgaagca caacatgatg   3540
aagtcctttc ttatatctgt gaaaatgcct tatataattt gtatgaatat gatagtcatt   3600
atttgttggc ttctgtcata ttatttttttc tagcattatt atccatattt gttggaatga   3660
tatatatgaa gtcgcgtaaa catagtgata agaaatgttc taaaaatctt atcaaaagta   3720
attatatacc agaaatggat gatggtatgg aagaaacaca acaactgcaa caagaaagaa   3780
gacaatattt cagagaatta tttggagaaa atttggaaaa gaattacgat cagcattttg   3840
tacaagattt tggtcaagat tttagacaag atttcaagct gggttcaaca ccagacttaa   3900
aacaatattc tgatatagat ttacaaaata agatacagca accggaaagg aaaaccgtaa   3960
agataattat taataacttt gaagatagaa agaaagagac cataagaaga ctactcaagg   4020
gattaaatta tgatggagaa aatgcaaaga aacatgattt cacgaatgaa agtattagca   4080
```

-continued atagtaggaa aaattttaaa ttctcaaaca atacagaaat gaaaaaaaat actataaaaa 4140
gtgaggacgt caaaatagca tctgacgata atgttaataa agcaatgaat caacttgatg 4200
atatgtttat gaaatgatat ataaaaaata tataacactt tcagttttat acaccttttt 4260
ggaatatata tatatatata ttttcatatt tatttattag taaataataa aattaccctt 4320
ttattttttt aaatattttc tttgttataa aatatcatat atattttttt aatttttatg 4380
tagcctattt attatatata tatatatata tataatatat atatatatat atatatatat 4440
ttatgtatat tttatttttt aatagtactc atttttttatg tgaaaacaca ttatcctctt 4500
ttttctgttt ttcattttat tttattttat ttatttattc attttttttt tttggtatac 4560
ataatagctt ttattagttc cataaatagt gttaaaaaaa aaaaaaaaaa a 4611

<210> SEQ ID NO 12
<211> LENGTH: 3678
<212> TYPE: DNA
<213> ORGANISM: Plasmodium yoelii

<400> SEQUENCE: 12
atgttgagaa cattttatgt tctatcctta atgctaattg aatttatact gcacaagggt 60
cagtataata agcatatttg ttcaaaaaat ttgaaaaaat ataattttgt tggtaagaaa 120
catcgaattt tggcaagtat tattgaagat agggaaaaac aagttgaaga tataacagat 180
ggttataagc ctatatttaa catttatgaa atatctgcag catttcacaa aaaaaaagat 240
atagcagata aaaaaaaaag acgaagatac ggaaaccaac aaagtataga aaacagaaga 300
attgctgaag aaaatgaaag acgtctatca aatcaattgg atgatataca atttattgaa 360
ttatctaata aatatcctaa tataggaaaa caaaattctc aacaaaataa agtaaataaa 420
ataaataatc aaaatggtgc atcgaattca aatgataata taagaaatga tgaggatgag 480
gatgagggtg aggatgaaga tgaagatgat gatttgatag aaggcaggaa agataattta 540
gaagaggatg atttagtaga aaaaaatggt gccaatttaa aaagggggaa catgcatgga 600
caggaagaaa aaaataaaaa tataaacaca actccaggca atgagaataa tagcaaaaat 660
gtaaatgata ataaaaaaag tggtataagt ctaaaagata aaattgacaa taatgagcaa 720
cataatagtg gtttaaaagg cacgacgaaa tatttagatg ataatataaa aacatataca 780
tttgaccatt ataaacttat aacaaattct gataatatat taaatgatat aaaagtagat 840
gcatcagata tttcaaagct aagtataaat agcttaagta tagaatataa tgaagtaaat 900
aaaaccgaat acacacacca aaggcatata gtattaacta ataaaggaaa tagacgatat 960
aaaatatttc taatgacaaa aaatccaaag tttacgaaaa cagaggatat tgaagaacct 1020
gaaatgagtt ttattcaaac agaaacagga gagaatacaa atgaaaaaga agacgaggaa 1080
aactatttga atgaaaattt gtatagtgga tttgggacta ttgattatga aaatggttat 1140
tcaaaaaaaa aaaaaaaaat taacagtgaa cacgcaagtg aacttaatga taaaattagt 1200
aacagccaaa acattgaaaa aagtgattct catgaaaatg aaaaatataa tcatggattt 1260
atagggaaga tacaaagttt ttttagtttt ttatccatcc caagtagcaa gaaagatgat 1320
agtattggaa gtgaaaaaaa atctgaggaa aggaacaatg tcgattctaa acctaaatta 1380
aataagaaac ctaatgatac ggccaaaaaa aataattcaa ataaaatttt gactgtagac 1440
aaagttacag atcaatatct attaaactta aagaataaaa atatgaaaga acaagaattg 1500
atattcattt tccatgggga tttagattta cattcgaaga agatgaaaac aattataaat 1560
gaagcaaatg ttaaatttac aaaatatata aatatgcatt ttaaagacgt taagaatata 1620
cgttatgata tatcatcacc aataaacttt gtgtgttttt ttattcctat aatttttgat 1680
atgagcaatt taaagatatt aaaagaggca ttaattatat tgcataatga gctcaagaat 1740
tatatcgata attggaattt ttcaaatact tatatagcat ttgataccga ttatgaaaat 1800
gaagatattg acaatgcaat gaataaatta aatgaaaata tgaaaaaata tattaaaaaa 1860
cccaaaaaat tatataatat aaaatattca tttttaagaa aaatgtgggg tctagaatca 1920
attttctctt tatccaaaaa tcgaaatcaa aaaaatgctg gaatagaaga aaaaattttg 1980
aacgcattac caaaagaatt gaaagagtat tcgacttgga atttatcttt tataagagta 2040
tttaatgctt ggcttttgtc tgggtatgga aataaaaatg taaagatatg tgttatagat 2100
tcaggggttg ataaaaacca tatagattta gcaaaaaata tatacacacc gaaatattca 2160
gatagatatg aaatgacaga tgattttttt gattttatgg ttaaaaatcc aatagataca 2220
tctgggcatg gtacacatgt ttctggaata gcagctgctt cggcaaattc tttaggtatg 2280
gttggtgttg ctcctgatgt caatttgata tctttacgat ttattgatgg agatagttat 2340
ggaggtagtt tccatgtaat taaagctata aatgtttgta tattaaacaa atcgccaatt 2400
attaatgcta gttggggttc tagaaattat gatacgaata tgttcttagc tattgaaaga 2460
ttaaaatata cttttaaggg gaaaggaaca gtttttatag ctgcagcagg aaatgaaaat 2520
aaaaacaacg atctttatcc tatataccct gctagttata aacttccaaa tgtttatagt 2580
gttggttcca tcaacaaatt cttacaaatt tcaccatttt ctaattatgg agctaacagt 2640
gtgcacattc ttgcaccagg acatcacata tattccacaa cacctatgaa cacatacaaa 2700
atgaatacag gtacttctat ggcagcccct catgtatcgg gagtagctgg attgatatat 2760
tcggtatgtc ataaacaagg atttatacct gaatctgatg aagttttaga tataataaca 2820
aggacatcta taaaaatagt atctaaggac aaaaaaacaa tacataatag tttaataaat 2880
gcagaagcag cagtattaac tacattactg ggaggtttat ggatgcaaat ggattgccat 2940
tttgctaagt tttatttaaa taaagatcaa caaaaaaaca ttcctgttgt attttcagca 3000
tataaagatg gaatgtatga atcagatata attataggaa ttcaacctga agattctaat 3060
tcaaaagaat atggagaaat tgtgattcct attaaaatat taacaaatcc caaattaaaa 3120
aattttaatt tatcaccaag agttggaaaa aaaatccaca ttgatgcaaa tgagtcaaat 3180
gatgatatat tatcatacat ttgtgaaaat gctttatata atttatatga gcatgacaac 3240
agttttttaa tttcatcatt gatattgttc tttataggaa ttatattaat cgctttagca 3300
tcgattgtgt ttttttaaa acatcatcaa agtaaacaac gagatgccga aaaatatatg 3360
catcaaaaaa tggtagatag ggcacatgga ataaaatata attttaagga tgcgggtgcc 3420
gatggtatta aaagaataaa tacaatggat gacaatataa acaatcaccg aaatactcag 3480
agatttacta ttgttcaaaa tgaagataat atgtatgtgc taaaaaaaaa aagttctatt 3540
caagcaaaat atgaaccacg caatgaattg gtaaaacgcc cacttgtaaa acgtccaatt 3600
gtaaagcatg cagatataaa tgtaaatttc aaaaatatag atgaattata cgaaccacaa 3660
aacaactcac cggaatag 3678

<210> SEQ ID NO 13
<211> LENGTH: 552
<212> TYPE: DNA
<213> ORGANISM: Plasmodium berghei
<220> FEATURE:
<221> NAME/KEY: misc_feature
<223> OTHER INFORMATION: Pbsub2-3'UTR

<400> SEQUENCE: 13
tagatgattc catcgagaaa aggaggagat aatacattgt agaatctttg tgagacacat 60
tgatctcaca tatgagtata tatatctcca aaaaatagta attaaaaaat tataatagtt 120
tttcctcaca atgatatagc ataatattgt tcatttattt ttttttattt tatgctttaa 180
taaattgttt ataaatattt ttttaatgta taatatgcat taaatgcata tttcgtattt 240
tttattttat atgtgtatgt atgactatat ttttatattt gtatatagtt tgttttataa 300
aattatataa taaactttaa atataaacat taatattttg cctttcaaaa gcataaagcg 360
ttttaataag catgtttaat tatttagaga atatattatc ctttaataat attatcatta 420
tattaattta tccttataaa ttaaagtagt taaatgtagt ggaaaagttt agcaatttaa 480
ttcccataaa acatattgag gaataattac tgttgatttt tcataactta ttttattata 540
tatatgacta tt 552

<210> SEQ ID NO 14
<211> LENGTH: 623
<212> TYPE: DNA
<213> ORGANISM: Plasmodium yoelii
<220> FEATURE:
<221> NAME/KEY: misc_feature
<223> OTHER INFORMATION: Pysub2-3'UTR

<400> SEQUENCE: 14
tagattattc caccgagaaa tgaggagaga atacattata gggtttttgt gagacacatt 60
gatctcacat atgagtatat attacacata tatttattta attatttgac attttcttaa 120
attttccttt ttttgtttta gaaaatatat gtatatatat ctccaaaaaa tagtaattaa 180
aaaattataa tagttttttt tcacaatgat atagcataat attgttcatt tattttttct 240
attttttgct ttaataaatt gtttataaat atattttttt ttaatatata atatgcatta 300
aatgcatgtt tcgtcttttt tattttatat ccgtatgact atatttttat atttgtatat 360
agtttgtttt ataaaattac ataatcacct ttaaatattg gcattaatgc ttttcctttt 420
aaaagcataa agcgttttaa taaacatgtt taattattta gagaaatata ttacccttta 480
aaaatcatta tattaattta tactttataa attaaagtag ttaaattagc ggcaaattta 540
gcaatttaat tcttataaaa cattgaggaa taaaattgtt gatttttcat gacttatttt 600
atttatgacc tatttttat tta 623

<210> SEQ ID NO 15
<211> LENGTH: 635
<212> TYPE: DNA
<213> ORGANISM: Plasmodium falciparum
<220> FEATURE:
<221> NAME/KEY: misc_feature
<223> OTHER INFORMATION: Pfsub2-3'UTR

<400> SEQUENCE: 15
tgatatataa aaaatatata acactttcag ttttatacac ctttttggaa tatatatata 60
tatatatttt catatttatt tattagtaaa taataaaaat taacccttttt attttttttaa 120 atattttctt tgttataaaa atatcatata tattttttta atttttatgt agcctattta 180
ttatatatat atatatatat ataaatatata tatatatata tatatatatt tatgtatatt 240
ttatttttta atagtactca ttttttatgt gaaaacacat tatcctcttt tttctgtttt 300
tcattttatt ttattttatt tatttattca tttttttttt ttggtataca taatagcttt 360
tattagttcc ataaatatgt taaaaaaaaa aaaatttaaa acaagtgaca tttaaacttg 420

-continued

```
atttattttt taacctttca aaaattaaat ttatattatt ttaaatatat caaggaacta    480

taataatata tgagaaaatt tccaaatact gataaaaaaa aaatattacg aaaaatattg    540

tttctaattt ttttttacaa aaataaaaaa aaaataagat tatatatata tatatatata    600

taatatagta tattttatat attaattttt aattt                               635
```